(12) United States Patent
Warren et al.

(10) Patent No.: US 8,600,489 B2
(45) Date of Patent: Dec. 3, 2013

(54) METHODS AND DEVICES FOR ACCURATELY CLASSIFYING CARDIAC ACTIVITY

(75) Inventors: Jay A. Warren, San Juan Capistrano, CA (US); Rick Sanghera, San Clemente, CA (US); Venugopal Allavatam, Oceanside, CA (US); Surekha Palreddy, Maplewood, MN (US)

(73) Assignee: Cameron Health, Inc., San Clemente, CA (US)

( * ) Notice: Subject to any disclaimer, the term of this patent is extended or adjusted under 35 U.S.C. 154(b) by 0 days.

(21) Appl. No.: 13/436,448

(22) Filed: Mar. 30, 2012

(65) Prior Publication Data

US 2012/0197334 A1  Aug. 2, 2012

Related U.S. Application Data

(63) Continuation of application No. 12/437,547, filed on May 7, 2009, now Pat. No. 8,160,687, which is a continuation-in-part of application No. 12/399,914, filed on Mar. 6, 2009, now Pat. No. 8,160,686.

(60) Provisional application No. 61/051,332, filed on May 7, 2008.

(51) Int. Cl.
*A61B 5/0452* (2006.01)

(52) U.S. Cl.
USPC .......................................... 600/516

(58) Field of Classification Search
USPC .............................. 600/516; 607/9
See application file for complete search history.

(56) References Cited

U.S. PATENT DOCUMENTS

| | | | |
|---|---|---|---|
| 4,184,493 A | 1/1980 | Langer et al. |
| 4,300,567 A | 11/1981 | Kolenik et al. |
| 4,407,288 A | 10/1983 | Langer et al. |
| 4,450,527 A | 5/1984 | Sramek |
| 4,457,315 A | 7/1984 | Bennish |
| 4,589,420 A | 5/1986 | Adams et al. |
| 4,595,009 A | 6/1986 | Leinders |
| 4,679,144 A | 7/1987 | Cox et al. |

(Continued)

FOREIGN PATENT DOCUMENTS

| | | |
|---|---|---|
| CN | 1819855 A | 8/2006 |
| CN | 1829554 A | 9/2006 |

(Continued)

OTHER PUBLICATIONS

"U.S. Appl. No. 12/399,901, Final Office Action mailed Apr. 11, 2013", 11 pgs.

(Continued)

*Primary Examiner* — Eric D. Bertram
(74) *Attorney, Agent, or Firm* — Schwegman Lundberg & Woessner, P.A.

(57) ABSTRACT

Methods, systems, and devices for signal analysis in an implanted cardiac monitoring and treatment device such as an implantable cardioverter defibrillator. In some examples, captured data including detected events is analyzed to identify likely overdetection of cardiac events. In some illustrative examples, when overdetection is identified, data may be modified to correct for overdetection, to reduce the impact of overdetection, or to ignore overdetected data. Several examples emphasize the use of morphology analysis using correlation to static templates and/or inter-event correlation analysis.

14 Claims, 15 Drawing Sheets

(56) References Cited

U.S. PATENT DOCUMENTS

| | | |
|---|---|---|
| 4,693,253 A | 9/1987 | Adams |
| 4,750,494 A | 6/1988 | King |
| 4,779,617 A | 10/1988 | Whigham |
| 4,940,054 A | 7/1990 | Grevis et al. |
| 4,979,110 A | 12/1990 | Albrecht et al. |
| 4,989,602 A | 2/1991 | Sholder et al. |
| 5,000,189 A | 3/1991 | Throne et al. |
| 5,105,810 A | 4/1992 | Collins et al. |
| 5,117,824 A | 6/1992 | Keimel et al. |
| 5,184,616 A | 2/1993 | Weiss |
| 5,193,535 A | 3/1993 | Bardy et al. |
| 5,215,098 A | 6/1993 | Steinhaus et al. |
| 5,217,021 A | 6/1993 | Steinhaus et al. |
| 5,240,009 A | 8/1993 | Williams |
| 5,271,411 A | 12/1993 | Ripley et al. |
| 5,273,049 A | 12/1993 | Steinhaus et al. |
| 5,280,792 A | 1/1994 | Leong et al. |
| 5,299,119 A | 3/1994 | Kraf et al. |
| 5,313,953 A | 5/1994 | Yomtov et al. |
| 5,331,966 A | 7/1994 | Bennett et al. |
| 5,339,820 A | 8/1994 | Henry et al. |
| 5,342,402 A | 8/1994 | Olson et al. |
| 5,342,407 A | 8/1994 | Dahl et al. |
| 5,351,696 A | 10/1994 | Riff et al. |
| 5,376,104 A | 12/1994 | Sakai et al. |
| 5,400,795 A | 3/1995 | Murphy et al. |
| 5,423,326 A | 6/1995 | Wang et al. |
| 5,447,519 A | 9/1995 | Peterson |
| 5,464,431 A | 11/1995 | Adams et al. |
| 5,470,342 A | 11/1995 | Mann et al. |
| 5,486,199 A | 1/1996 | Kim et al. |
| 5,513,644 A | 5/1996 | McClure et al. |
| 5,522,852 A | 6/1996 | White et al. |
| 5,534,019 A | 7/1996 | Paspa |
| 5,545,186 A | 8/1996 | Olson et al. |
| 5,558,098 A | 9/1996 | Fain |
| 5,564,430 A | 10/1996 | Jacobson et al. |
| 5,607,455 A | 3/1997 | Armstrong |
| 5,620,466 A | 4/1997 | Haefner et al. |
| 5,658,317 A | 8/1997 | Haefner et al. |
| 5,676,690 A | 10/1997 | Noren |
| 5,685,315 A | 11/1997 | McClure et al. |
| 5,702,425 A | 12/1997 | Wickham |
| 5,709,215 A | 1/1998 | Perttu et al. |
| 5,755,738 A | 5/1998 | Kim et al. |
| 5,776,168 A | 7/1998 | Gunderson |
| 5,779,645 A | 7/1998 | Olson et al. |
| 5,817,134 A | 10/1998 | Greenhut et al. |
| 5,827,197 A | 10/1998 | Bocek et al. |
| 5,857,977 A | 1/1999 | Caswell et al. |
| 5,891,048 A | 4/1999 | Nigam et al. |
| 5,991,657 A | 11/1999 | Kim |
| 6,029,086 A | 2/2000 | Kim et al. |
| 6,041,251 A | 3/2000 | Kim et al. |
| 6,047,210 A | 4/2000 | Kim et al. |
| 6,052,617 A | 4/2000 | Kim |
| 6,058,328 A | 5/2000 | Levine et al. |
| 6,095,987 A | 8/2000 | Shmulewitz et al. |
| 6,115,628 A | 9/2000 | Stadler et al. |
| 6,144,879 A | 11/2000 | Gray |
| 6,148,230 A | 11/2000 | Kenknight |
| 6,223,078 B1 | 4/2001 | Marcovecchio |
| 6,230,055 B1 | 5/2001 | Sun et al. |
| 6,236,882 B1 | 5/2001 | Lee et al. |
| 6,240,313 B1 | 5/2001 | Esler |
| 6,266,554 B1 | 7/2001 | Hsu et al. |
| 6,280,462 B1 | 8/2001 | Hauser et al. |
| 6,308,095 B1 | 10/2001 | Hsu et al. |
| 6,334,071 B1 | 12/2001 | Lu |
| 6,377,844 B1 | 4/2002 | Graen et al. |
| 6,381,493 B1 | 4/2002 | Stadler et al. |
| 6,393,316 B1 | 5/2002 | Gillberg et al. |
| 6,397,100 B2 | 5/2002 | Stadler et al. |
| 6,411,844 B1 | 6/2002 | Kroll et al. |
| 6,438,410 B2 | 8/2002 | Hsu et al. |
| 6,449,503 B1 | 9/2002 | Hsu |
| 6,493,579 B1 | 12/2002 | Gilkerson et al. |
| 6,493,584 B1 | 12/2002 | Lu |
| 6,505,068 B2 | 1/2003 | Bonnet et al. |
| 6,516,225 B1 | 2/2003 | Florio |
| 6,561,984 B1 | 5/2003 | Turcott |
| 6,567,691 B1 | 5/2003 | Stadler |
| 6,574,505 B1 | 6/2003 | Warren |
| 6,575,912 B1 | 6/2003 | Turcott |
| 6,587,720 B2 | 7/2003 | Hsu et al. |
| 6,625,490 B1 | 9/2003 | McClure et al. |
| 6,643,549 B1 | 11/2003 | Bradley et al. |
| 6,647,292 B1 | 11/2003 | Bardy et al. |
| 6,684,100 B1 | 1/2004 | Sweeney et al. |
| 6,699,200 B2 | 3/2004 | Cao et al. |
| 6,708,058 B2 | 3/2004 | Kim et al. |
| 6,708,062 B2 | 3/2004 | Ericksen et al. |
| 6,721,597 B1 | 4/2004 | Bardy et al. |
| 6,728,572 B2 | 4/2004 | Hsu et al. |
| 6,731,978 B2 | 5/2004 | Olson et al. |
| 6,745,068 B2 | 6/2004 | Koyrakh et al. |
| 6,754,528 B2 | 6/2004 | Bardy et al. |
| 6,889,079 B2 | 5/2005 | Bocek et al. |
| 6,892,092 B2 | 5/2005 | Palreddy et al. |
| 6,909,916 B2 | 6/2005 | Spinelli et al. |
| 6,950,702 B2 | 9/2005 | Sweeney |
| 7,016,730 B2 | 3/2006 | Ternes |
| 7,020,523 B1 | 3/2006 | Lu et al. |
| 7,027,856 B2 | 4/2006 | Zhou et al. |
| 7,027,858 B2 | 4/2006 | Cao et al. |
| 7,027,862 B2 | 4/2006 | Dahl et al. |
| 7,031,764 B2 | 4/2006 | Schwartz et al. |
| 7,062,314 B2 | 6/2006 | Zhu et al. |
| 7,062,315 B2 | 6/2006 | Koyrakh et al. |
| 7,062,322 B2 | 6/2006 | Stadler et al. |
| 7,076,289 B2 | 7/2006 | Sarkar et al. |
| 7,085,599 B2 | 8/2006 | Kim et al. |
| 7,103,412 B1 * | 9/2006 | Kroll .............................. 607/17 |
| 7,117,035 B2 | 10/2006 | Wagner et al. |
| 7,123,954 B2 | 10/2006 | Narayan et al. |
| 7,149,575 B2 | 12/2006 | Ostroff et al. |
| 7,162,301 B2 | 1/2007 | Kim et al. |
| 7,167,747 B2 | 1/2007 | Gunderson et al. |
| 7,184,815 B2 | 2/2007 | Kim et al. |
| 7,184,818 B2 | 2/2007 | Kim et al. |
| 7,191,004 B2 | 3/2007 | Kim et al. |
| 7,194,302 B2 | 3/2007 | Bardy et al. |
| 7,218,966 B2 | 5/2007 | Haefner et al. |
| 7,236,819 B2 | 6/2007 | Brockway et al. |
| 7,248,921 B2 | 7/2007 | Palreddy et al. |
| 7,266,409 B2 | 9/2007 | Gunderson |
| 7,283,863 B2 | 10/2007 | Gunderson et al. |
| 7,302,294 B2 | 11/2007 | Kamath et al. |
| 7,330,757 B2 | 2/2008 | Ostroff et al. |
| 7,346,392 B2 | 3/2008 | KenKnight |
| 7,376,458 B2 | 5/2008 | Palreddy et al. |
| 7,379,772 B2 | 5/2008 | Bardy et al. |
| 7,386,342 B1 | 6/2008 | Falkenberg et al. |
| 7,392,085 B2 | 6/2008 | Warren et al. |
| 7,444,182 B2 | 10/2008 | Ostroff et al. |
| 7,447,540 B1 | 11/2008 | Nabutovsky et al. |
| 7,467,009 B2 | 12/2008 | Palreddy et al. |
| 7,477,935 B2 | 1/2009 | Palreddy et al. |
| 7,496,408 B2 | 2/2009 | Ghanem et al. |
| 7,496,409 B2 | 2/2009 | Greenhut et al. |
| 7,499,750 B2 | 3/2009 | Haefner et al. |
| 7,522,959 B2 | 4/2009 | Hauser et al. |
| 7,546,159 B1 | 6/2009 | Nabutovsky et al. |
| 7,555,335 B2 | 6/2009 | Kamath et al. |
| 7,559,900 B2 | 7/2009 | Gillberg |
| 7,567,835 B2 | 7/2009 | Gunderson et al. |
| 7,570,997 B2 | 8/2009 | Lovett et al. |
| 7,593,771 B2 | 9/2009 | Yonce et al. |
| 7,623,913 B2 | 11/2009 | Phillips |
| 7,623,916 B2 | 11/2009 | Julian |
| 7,655,014 B2 | 2/2010 | Ko et al. |
| 7,682,316 B2 | 3/2010 | Anderson et al. |
| 7,684,864 B2 | 3/2010 | Olson et al. |
| 7,715,906 B2 | 5/2010 | Krause et al. |

(56) References Cited

U.S. PATENT DOCUMENTS

| | | |
|---|---|---|
| 7,734,345 B2 | 6/2010 | Cinbis |
| 7,761,142 B2 | 7/2010 | Ghanem et al. |
| 7,774,049 B2 | 8/2010 | Ghanem et al. |
| 7,783,354 B2 | 8/2010 | Gunderson |
| 7,792,571 B2 | 9/2010 | Sweeney et al. |
| 7,797,036 B2 | 9/2010 | Zhang et al. |
| 7,801,594 B1 | 9/2010 | Higham |
| 7,865,233 B2 | 1/2011 | Haefner |
| 7,894,894 B2 | 2/2011 | Stadler et al. |
| 7,904,142 B2 | 3/2011 | Kim et al. |
| 7,904,153 B2 | 3/2011 | Greenhut et al. |
| 7,907,993 B2 | 3/2011 | Ghanem et al. |
| 2003/0204215 A1 | 10/2003 | Gunderson et al. |
| 2004/0049120 A1 | 3/2004 | Cao et al. |
| 2004/0215239 A1 | 10/2004 | Favet et al. |
| 2004/0215240 A1 | 10/2004 | Lovett et al. |
| 2004/0220628 A1 | 11/2004 | Wagner |
| 2004/0230229 A1 | 11/2004 | Lovett et al. |
| 2005/0107838 A1 | 5/2005 | Lovett et al. |
| 2005/0131464 A1 | 6/2005 | Heinrich et al. |
| 2005/0154421 A1 | 7/2005 | Ousdigian et al. |
| 2006/0116595 A1 | 6/2006 | Palreddy et al. |
| 2006/0116725 A1 | 6/2006 | Palreddy et al. |
| 2006/0122676 A1 | 6/2006 | Ko |
| 2006/0167502 A1 | 7/2006 | Haefner |
| 2006/0167503 A1 | 7/2006 | Warren et al. |
| 2006/0167504 A1 | 7/2006 | Warren et al. |
| 2006/0235476 A1 | 10/2006 | Gunderson |
| 2006/0241701 A1 | 10/2006 | Markowitz et al. |
| 2007/0032829 A1 | 2/2007 | Ostroff |
| 2007/0049975 A1 | 3/2007 | Cates et al. |
| 2007/0135847 A1 | 6/2007 | Kenknight |
| 2007/0142736 A1 | 6/2007 | Cazares et al. |
| 2007/0156190 A1 | 7/2007 | Cinbis |
| 2007/0179539 A1 | 8/2007 | Degroot et al. |
| 2007/0179540 A1 | 8/2007 | Stegemann et al. |
| 2007/0232944 A1 | 10/2007 | Ghanem et al. |
| 2007/0232945 A1 | 10/2007 | Kleckner et al. |
| 2007/0232948 A1 | 10/2007 | Stadler et al. |
| 2007/0233198 A1 | 10/2007 | Ghanem et al. |
| 2007/0276445 A1 | 11/2007 | Sanghera et al. |
| 2008/0015647 A1 | 1/2008 | Palreddy et al. |
| 2008/0077030 A1 | 3/2008 | Ostroff et al. |
| 2008/0086174 A1 | 4/2008 | Libbus et al. |
| 2008/0091242 A1 | 4/2008 | Kamath et al. |
| 2008/0132965 A1 | 6/2008 | Ostroff et al. |
| 2008/0161870 A1 | 7/2008 | Gunderson |
| 2008/0172098 A1 | 7/2008 | Gunderson |
| 2008/0183085 A1 | 7/2008 | Van Oort et al. |
| 2008/0188901 A1 | 8/2008 | Sanghera et al. |
| 2008/0215110 A1 | 9/2008 | Gunderson |
| 2008/0221632 A1 | 9/2008 | Bardy et al. |
| 2008/0228093 A1 | 9/2008 | Dong et al. |
| 2008/0243200 A1 | 10/2008 | Scinicariello et al. |
| 2008/0262559 A1 | 10/2008 | Zhang et al. |
| 2008/0275516 A1 | 11/2008 | Ghanem et al. |
| 2008/0275517 A1 | 11/2008 | Ghanem et al. |
| 2008/0275519 A1 | 11/2008 | Ghanem et al. |
| 2008/0275521 A1 | 11/2008 | Warren et al. |
| 2008/0288009 A1 | 11/2008 | Kim et al. |
| 2009/0036788 A1 | 2/2009 | Nabutovsky et al. |
| 2009/0043352 A1 | 2/2009 | Brooke et al. |
| 2009/0054796 A1 | 2/2009 | Sanghera et al. |
| 2009/0054938 A1 | 2/2009 | Ostroff et al. |
| 2009/0093731 A1 | 4/2009 | Palreddy et al. |
| 2009/0156957 A1 | 6/2009 | Linder et al. |
| 2009/0157128 A1 | 6/2009 | Seim et al. |
| 2009/0157132 A1 | 6/2009 | Linder et al. |
| 2009/0157137 A1 | 6/2009 | Gilkerson et al. |
| 2009/0187227 A1 | 7/2009 | Palreddy et al. |
| 2009/0228057 A1 | 9/2009 | Allavatam et al. |
| 2009/0240157 A1 | 9/2009 | Lian et al. |
| 2009/0240300 A1 | 9/2009 | Lian et al. |
| 2009/0259271 A1 | 10/2009 | Allavatam et al. |
| 2010/0004713 A1 | 1/2010 | Warren et al. |
| 2010/0094369 A1 | 4/2010 | Allavatam et al. |
| 2010/0152798 A1 | 6/2010 | Sanghera et al. |
| 2010/0152799 A1 | 6/2010 | Sanghera et al. |
| 2010/0185109 A1 | 7/2010 | Zhang et al. |
| 2010/0331904 A1 | 12/2010 | Warren et al. |
| 2011/0098585 A1 | 4/2011 | Warren et al. |
| 2011/0098775 A1 | 4/2011 | Allavatam et al. |
| 2013/0006085 A1 | 1/2013 | Allavatam et al. |

FOREIGN PATENT DOCUMENTS

| | | |
|---|---|---|
| CN | 1915166 A | 2/2007 |
| CN | 1985750 A | 6/2007 |
| CN | 101065059 A | 10/2007 |
| EP | 0554208 A2 | 8/1993 |
| EP | 2455132 A1 | 5/2012 |
| WO | WO-2004105871 A1 | 12/2004 |
| WO | WO-2009111764 A2 | 9/2009 |
| WO | WO-2009111764 A3 | 9/2009 |
| WO | WO-2009111766 A2 | 9/2009 |
| WO | WO-2009111766 A3 | 9/2009 |
| WO | WO-2009137726 A2 | 11/2009 |
| WO | WO-2009137726 A3 | 11/2009 |

OTHER PUBLICATIONS

"U.S. Appl. No. 12/399,901, Non Final Office Action mailed Sep. 17, 2012", 44 pgs.

"U.S. Appl. No. 12/399,901, Response filed Apr. 6, 2012 to Restriction Requirement mailed Mar. 6, 2012", 25 pgs.

"U.S. Appl. No. 12/399,901, Response filed Dec. 17, 2012 to Non Final Office Action mailed Sep. 17, 2012", 16 pgs.

"U.S. Appl. No. 12/399,901, Restriction Requirement mailed Mar. 6, 2012", 8 pgs.

"U.S. Appl. No. 12/399,914, Non-Final Office Action mailed Oct. 21, 2011", 34 pgs.

"U.S. Appl. No. 12/399,914, Notice of Allowance mailed Feb. 14, 2012", 5 pgs.

"U.S. Appl. No. 12/399,914, Response filed Oct. 7, 2011 to Restriction Requirement mailed Sep. 9, 2011", 11 pgs.

"U.S. Appl. No. 12/399,914, Response received Jan. 13, 2012 to Non-Final Office Action mailed Oct. 21, 2011", 8 pgs.

"U.S. Appl. No. 12/399,914, Restriction Requirement mailed Sep. 9, 2011", 6 pgs.

"U.S. Appl. No. 12/437,547, Non-Final Office Action mailed Nov. 10, 2011", 34 pgs.

"U.S. Appl. No. 12/437,547, Notice of Allowance mailed Feb. 15, 2012", 5 pgs.

"U.S. Appl. No. 12/437,547, Response filed Jan. 27, 2012 to Non-Final Office Action mailed Nov. 10, 2011", 6 pgs.

"U.S. Appl. No. 12/437,547, Response filed Oct. 10, 2011 to Restriction Requirement mailed Sep. 9, 2011", 12 pgs.

"U.S. Appl. No. 12/437,547, Restriction Requirement mailed Sep. 9, 2011", 5 pgs.

"U.S. Appl. No. 12/637,438, Non-Final Office Action mailed Dec. 7, 2011", 34 pgs.

"U.S. Appl. No. 12/637,438, Notice of Allowance mailed May 16, 2012", 5 pgs.

"U.S. Appl. No. 12/637,438, Response filed Feb. 29, 2012 to Non-Final Office Action mailed Dec. 7, 2011", 11 pgs.

"U.S. Appl. No. 12/637,438, Response filed Nov. 18, 2011 to Restriction Requirement mailed Oct. 21, 2011", 8 pgs.

"U.S. Appl. No. 12/637,438, Restriction Requirement mailed Oct. 21, 2011", 7 pgs.

"U.S. Appl. No. 13/436,398, Restriction Requirement mailed Mar. 15, 2013", 6 pgs.

"U.S. Appl. No. 13/607,168, Non Final Office Action mailed Mar. 26, 2013", 7 pgs.

"U.S. Appl. No. 13/607,168, Response filed Mar. 14, 2013 to Restriction Requirement mailed Feb. 27, 2013", 6 pgs.

"U.S. Appl. No. 13/607,168, Restriction Requirement mailed Feb. 27, 2013", 5 pgs.

"Chinese Application Serial No. 200980116877.4, Office Action mailed Jan. 30, 2013", w/English translation, 17 pgs.

(56) References Cited

OTHER PUBLICATIONS

"Chinese Application Serial No. 200980116886.3, Office Action mailed Dec. 13, 2012", w/English Translation, 16 pgs.
"Chinese Application Serial No. 200980125869.6, Office Action mailed Jan. 10, 2013", (With English Translation), 12 pgs.
"European Application Serial No. 09717667.1, Office Action mailed Dec. 16, 2011", 4 pgs.
"European Application Serial No. 09717667.1, Response filed Apr. 26, 2012 to Office Action mailed Dec. 16, 2011", 44 pgs.
"European Application Serial No. 09717991.5, Office Action mailed Dec. 16, 2011", 4 pgs.
"European Application Serial No. 09717991.5, Response filed Apr. 26, 2012 to Office Action mailed Dec. 16, 2011", 41 pgs.
"European Application Serial No. 09743712.3, Office Action mailed Jun. 8, 2011", 3 pgs.
"European Application Serial No. 09743712.3, Response filed Aug. 10, 2011 to Office Action mailed Jun. 8, 2011", 9 pgs.
"European Application Serial No. 12151591.0, European Search Report mailed Mar. 21, 2012", 6 pgs.
"European Application Serial No. 12151591.0, Response filed Oct. 26, 2012 to European Search Report mailed Mar. 21, 2012", 10 pgs.
"European Application Serial No. 12151593.6, European Search Report mailed Mar. 21, 2012", 7 pgs.
"European Application Serial No. 12151593.6, Response filed Oct. 26, 2012 to European Search Report mailed Mar. 21, 2012", 13 pgs.
"European Application Serial No. 12151595.1, European Search Report mailed Mar. 21, 2012", 6 pgs.
"European Application Serial No. 12151595.1, Response filed Oct. 26, 2012 to European Search Report mailed Mar. 21, 2012", 9 pgs.
"European Application Serial No. 12189307.7, Extended European Search Report mailed Mar. 1, 2013", 6 pgs.
"European Application Serial No. 12189311.9, Extended European Search Report mailed Mar. 1, 2013", 6 pgs.
"International Application Serial No. PCT/US2009/036432, International Report on Patentability mailed Sep. 22, 2009".
"International Application Serial No. PCT/US2009/036432, International Search Report mailed Sep. 22, 2009", 5 pgs.
"International Application Serial No. PCT/US2009/036432, International Written Opinion mailed Sep. 7, 2010", 11 pgs.
"International Application Serial No. PCT/US2009/036434, International Preliminary Report on Patentability mailed Sep. 7, 2010", 14 pgs.
"International Application Serial No. PCT/US2009/036434, International Search Report mailed Sep. 22, 2009", 7 pgs.
"International Application Serial No. PCT/US2009/036434, International Written Opinion mailed Sep. 7, 2010", 13 pgs.
"International Application Serial No. PCT/US2009/043213, International Report on Patentability mailed Nov. 9, 2010", 13 pgs.
"International Application Serial No. PCT/US2009/043213, International Search Report mailed Dec. 1, 2009", 7 pgs.
"International Application Serial No. PCT/US2009/043213, International Written Opinion mailed Nov. 7, 2010", 12 pgs.
"Methods and Devices for Identifying and Correcting Overdetection of Cardiac Events", U.S. Appl. No. 61/051,332, filed May 7, 2008, 62 pgs.
"QT Interval", Wikipedia, [Online]. Retrieved from the Internet: <URL: http://en.wikipedia.org/wiki/QT_interval>, (Accessed May 11, 2011), 5 pgs.
Gunderson, et al., "An Algorithm to Predict Implantable Cardioverter-Defibrillator Lead Failure", JACC, vol. 44, No. 9,, (Nov. 2004), 1898-902.
Olson, Walter, et al., "Onset and Stability for Ventricular Tachyarrhythmia Detection in an Implantable Pacer-Cardioverter-Defibrillator", IEEE, (1987), 167-170.
Schuder, John C, "The Role of an Engineering Oriented Medical Research Group in Developing Improved Methods & Devices for Achieving Ventricular Defibrillation: The University of Missouri Experience", PACE vol. 16, Part I,, (Jan. 1993), 95-124.
Schwake, "Komplikationen mit Sonden bei 340 Patienten mit einem implantierbaren Kardioverter/Defibrilator", Z Kardiol 88, (1999), 559-565.
Swerdlow, C. D, et al., "Advanced ICD Troubleshooting: Part I.", accessed and printed Jul. 7, 2009, indicates publication Jan. 9, 2006 (publication date not confirmed)., [Online]. Retrieved from the Internet: <http://www.medscape.com/viewarticle/520588_print>, (Accessed Jul. 7, 2009), 1322-46.
Throne, Robert D, et al., "A Comparison of Four New Time-Domain Techniques for Discriminating Monomorphic Ventricular Tachycardia from Sinus Rhythm Using Ventricular Waveform Morphology", IEEE Transactions on Biomedical Engineering, vol. 38, No. 6, (Jun. 1991), 561-570.
"U.S. Appl. No. 13/436,398, Non Final Office Action mailed May 9, 2013", 6 pgs.
"European Application Serial No. 12151591.0, Office Action mailed Dec. 19, 2012", 5 pgs.
"European Application Serial No. 12151593.6, Office Action mailed May 7, 2012", 2 pgs.
"European Application Serial No. 12151593.6, Office Action mailed Dec. 19, 2012", 5 pgs.
"European Application Serial No. 12151593.6, Response filed Apr. 19, 2013 to Office Action mailed Dec. 19, 2012", 8 pgs.

\* cited by examiner

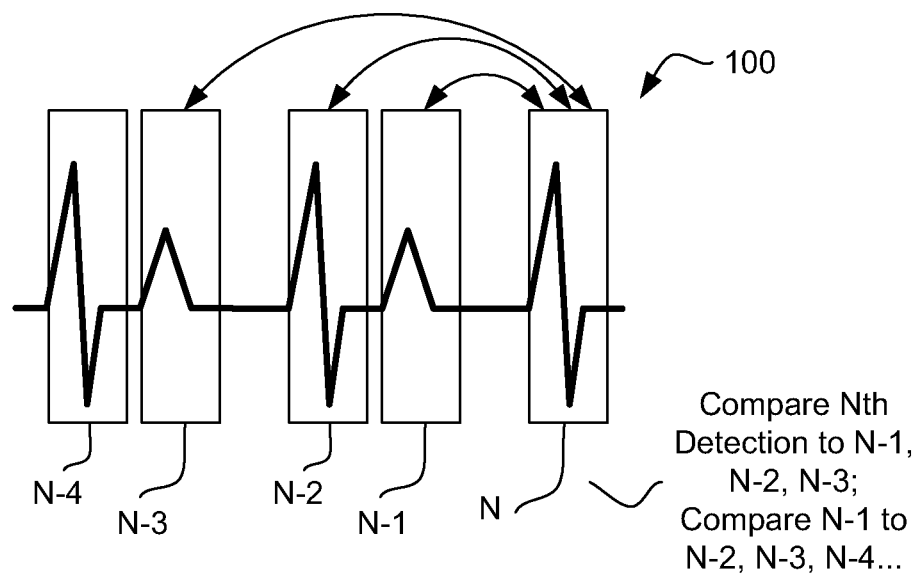
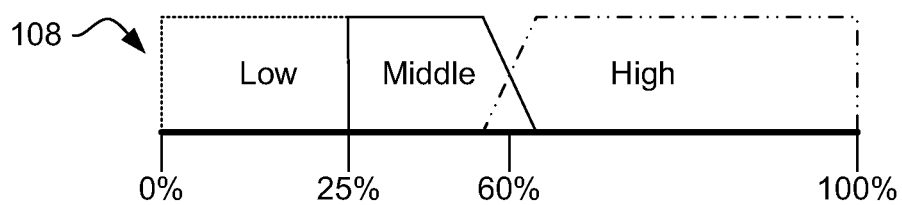
FIG. 4

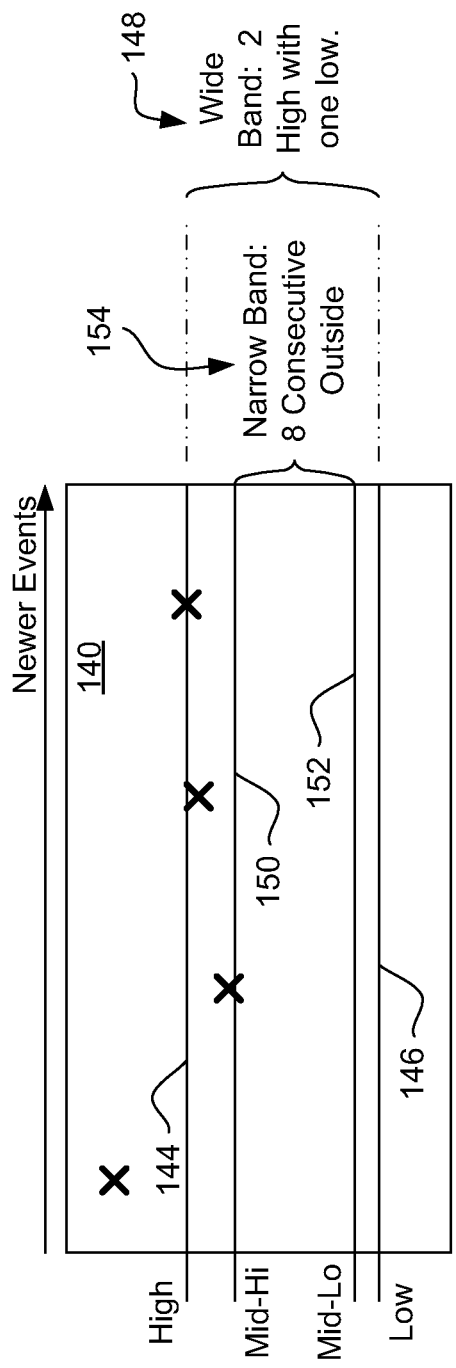
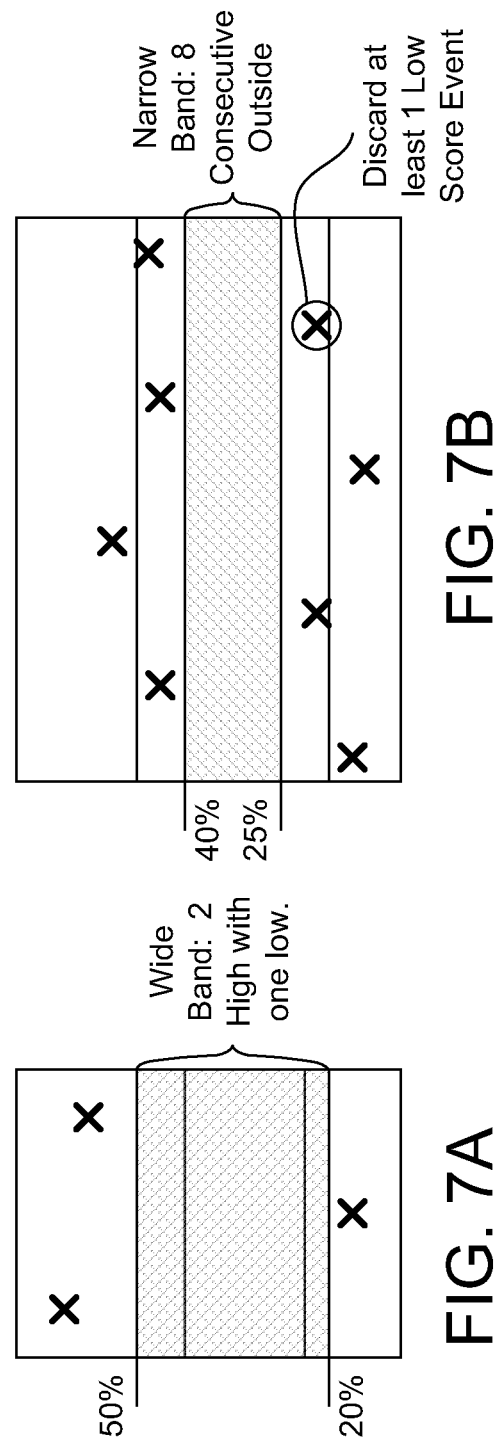
FIG. 6
FIG. 7A
FIG. 7B

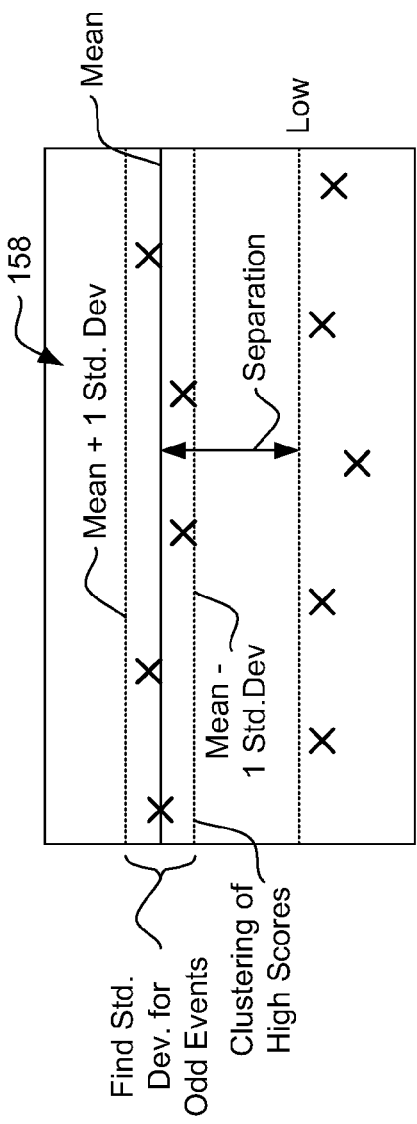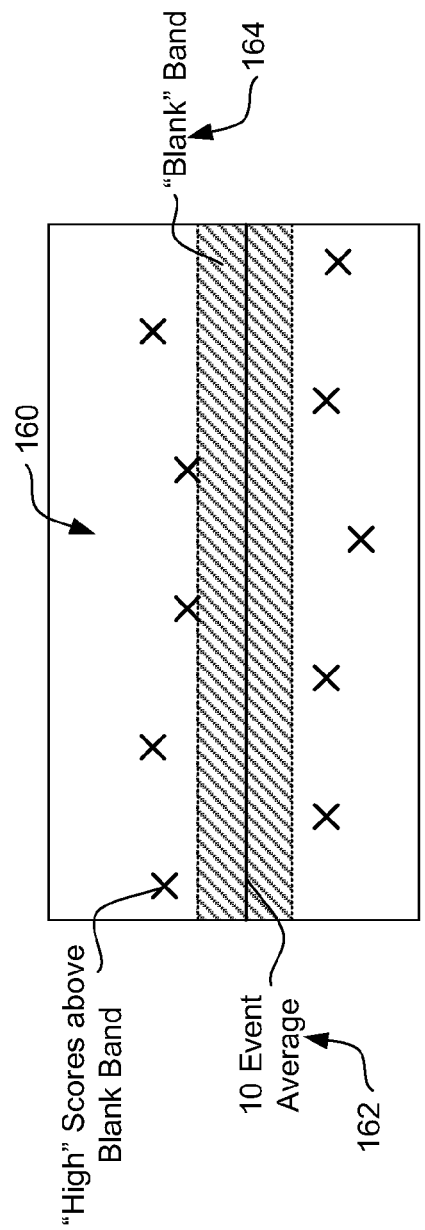

METHODS AND DEVICES FOR ACCURATELY CLASSIFYING CARDIAC ACTIVITY

RELATED APPLICATIONS

The present application is a continuation of U.S. patent application Ser. No. 12/437,547, filed May 7, 2009 and published as US Patent Application Publication Number 2010-0004713, now issued as U.S. Pat. No. 8,160,687, which claims the benefit of and priority to U.S. Provisional Patent Application No. 61/051,332, filed May 7, 2008 and titled METHODS AND DEVICES FOR IDENTIFYING AND CORRECTING OVERDETECTION OF CARDIAC EVENTS, and which is also a Continuation-In-Part of U.S. patent application Ser. No. 12/399,914, filed Mar. 6, 2009, published as U.S. Patent Application Publication Number 2009-0259271, now issued as U.S. Pat. No. 8,160,686, and titled METHODS AND DEVICES FOR ACCURATELY CLASSIFYING CARDIAC ACTIVITY, the disclosures of which are incorporated herein by reference.

The present application is related to U.S. patent application Ser. No. 12/399,901, filed Mar. 6, 2009 and titled ACCURATE CARDIAC EVENT DETECTION IN AN IMPLANTABLE CARDIAC STIMULUS DEVICE, published as US Patent Application Publication Number 2009-0228057, which claims the benefit of and priority to U.S. Provisional Patent Application No. 61/034,938, filed Mar. 7, 2008, the disclosures of which are incorporated herein by reference.

FIELD

The present invention relates generally to implantable medical device systems that sense and analyze cardiac signals. More particularly, the present invention relates to implantable medical devices that capture cardiac signals within an implantee's body in order to classify cardiac activity as likely benign or malignant.

BACKGROUND

Implantable cardiac devices typically sense cardiac electrical signals in an implantee and classify the implantee's cardiac rhythm as normal/benign or malignant. Illustrative malignant rhythms may include ventricular fibrillation and/or ventricular tachyarrhythmia. The accuracy with which an implantable medical device analyzes captured signals determines how well it makes therapy and other decisions.

New and/or alternative methods and devices for cardiac signal analysis are desired.

SUMMARY

Some illustrative embodiments relate to the use of correlation analysis to identify overdetection of cardiac events. In one example, a High-Low-High pattern of correlation relative to a template is sought. The template may be a static template, it may be a representation of a recent captured event, or it may be an average of several recent captured events. In another example, multiple boundaries for High correlation are defined, wherein a first, higher boundary (requiring greater correlation) allows identification of overdetection based on a smaller set of detected events than a second, lower boundary. In one embodiment, a shorter sequence of High-Low-High is sufficient with the first boundary, while a longer sequence of five or more (for example, eight) alternating events is required for the second boundary. In another embodiment, definitions of High and Low correlation are adapted to the particular signals by using average values for subsets of detected event correlations to establish boundaries.

In another embodiment, correlation analysis is performed multiple times for a given template and detected event by shifting the alignment of the template and the detected event to maximize the correlation score of the analysis. Such shifting may adjust the alignment by one or more samples away from the identified fiducial points for analysis. In another embodiment, stored templates are modified in order to accommodate changes in morphology for selected portions of the signal. In yet another embodiment, multiple features of the template and/or signal are identified and multiple correlation scores are calculated using several different features as alignment points.

When identified, overdetection can be corrected by modifying stored data in order to impact rate analysis. In one such embodiment, data correction is inhibited if the intervals surrounding a likely overdetection are longer than a predetermined threshold. In some embodiments, overdetection correction is inhibited if interval analysis relating to a likely overdetection indicates that it is unlikely to be a particular type of overdetection. In one such embodiment, the intervals surrounding a likely overdetection are analyzed to determine whether an accepted formula for estimating expected QT intervals is met and, if not, the method determines that the likely overdetection is not a T-wave, and so no data correction occurs.

BRIEF DESCRIPTION OF THE DRAWINGS

FIG. 4 shows an example of inter-event correlation comparisons;

FIG. 6 shows an analytical approach to short series and long series correlation analysis;

FIGS. 7A-7B illustrate examples of applying the analytical approach of FIG. 6 to series of correlation analyses;

FIGS. 8A-8B illustrate examples of tailoring correlation analysis to observed levels of correlation to a template;

DETAILED DESCRIPTION

Figure 1:
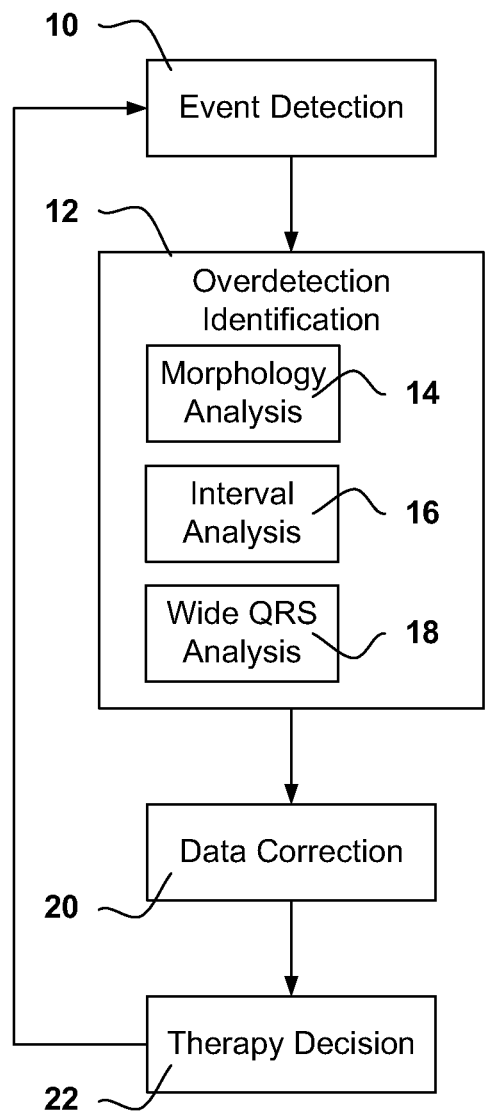
FIG. 1 is a block diagram for an illustrative method of identifying overdetection and taking corrective action.

The following detailed description should be read with reference to the drawings. The drawings, which are not necessarily to scale, depict illustrative embodiments and are not intended to limit the scope of the invention. Some of the following examples and explanations include references to issued patents and pending patent applications. These references are for illustrative purposes and are not intended to limit the present invention to the particular methods or structures from those referenced patents and patent applications.

Unless implicitly required or explicitly stated, the methods below do not require any particular order of steps. It should be understood that when the following examples refer to a "current event," in some embodiments, this means the most recently detected cardiac event is being analyzed. However, this need not be the case, and some embodiments perform analysis that is delayed by one or more detections and or a fixed period of time. Choices shown regarding use of rectified/unrectified signals are merely illustrative, and may be changed if desired.

The nomenclature used herein indicates that a signal is sensed by an implantable cardiac device system, events are detected in the sensed signal, and cardiac activity is classified by use of the detected events (detections). Rhythm classification includes the identification of malignant rhythms, such as ventricular fibrillation or certain tachyarrhythmias, for example. Implantable therapy systems make therapy/stimulus decisions in reliance upon the classification of the cardiac rhythm.

In an illustrative example, a detected event is detected by comparing received signals to a detection threshold, which is defined by a detection profile. Any suitable detection profile may be used. Detected events are separated by intervals. Several intervals can be used to generate an average interval across a selected number of intervals, from which cardiac rate can be calculated. For example, four, eight or sixteen intervals may be used to estimate cardiac event rate as a function of average interval.

A cardiac electrogram includes several portions (often referenced as "waves") that, according to well known convention, are labeled with letters including P, Q, R, S, and T, each of which corresponds to particular physiological events. It is typical to design detection algorithms to sense the R-wave, though any portion of the cardiac cycle, if repeatedly detected, can be used to generate a beat rate. If morphology (shape) analysis is used in addition to heart rate, the system may capture and/or analyze the portion of the cycle that includes the Q, R and S waves, referred to as the QRS complex. Other portions of the patient's cardiac cycle, such as the P-wave and T-wave, are often treated as artifacts that are not sought for the purpose of estimating heart rate, though this need not be the case.

Typically, for purposes of ascertaining rate each cardiac cycle is counted only once. Overdetection (such as a double or triple detection) may occur if the device declares more than one detected event within a single cardiac cycle. Overdetection may occur if more than one portion of a single cardiac cycle is detected, or if noise causes an event to be declared when no cardiac event has taken place, for example, due to external therapy or noise, pacing artifact, skeletal muscle noise, electro-therapy, etc.

If one cardiac cycle takes place and a detection algorithm declares multiple detected events, overdetection has occurred. If the heart rate is then calculated by counting each of these detections, overcounting occurs. Calculated heart rates may be used alone or in combination with other factors to classify cardiac rhythms as malignant or benign. Overcounting in reliance on overdetected events can result in erroneously high rate calculation. Miscalculation of heart rate can lead to incorrect rhythm classification and therapy decisions. Some of these concepts are further discussed and developed in U.S. patent application Ser. No. 12/399,914, titled METHODS AND DEVICES FOR ACCURATELY CLASSIFYING CARDIAC ACTIVITY, published as US Patent Application Publication Number 2009-0259271 and U.S. patent application Ser. No. 12/399,901, titled ACCURATE CARDIAC EVENT DETECTION IN AN IMPLANTABLE CARDIAC STIMULUS DEVICE, published as US Patent Application Publication Number 2009-0228057.

FIG. 1 is a process flow diagram for an illustrative method of identifying overdetection and taking corrective action. The illustrative method begins with event detection 10, where a received cardiac signal is captured and compared to a detection threshold until the received signal crosses the detection threshold, resulting in declaration of a detected event.

Next, the method performs an overdetection identification step 12. This may include one or more of several analysis methods including, as illustratively shown, morphology analysis 14, interval analysis 16 and wide QRS analysis 18. Following overdetection identification 12, if one or more overdetections are identified, the method corrects data, as shown at 20. If no data correction is needed at step 20, this step may be bypassed.

Finally, the method includes a therapy decision, as shown at 22. A therapy decision 22 may classify a cardiac rhythm of the implantee and determines whether/when therapy is to be delivered. The method then iterates to event detection 10.

Figure 15:
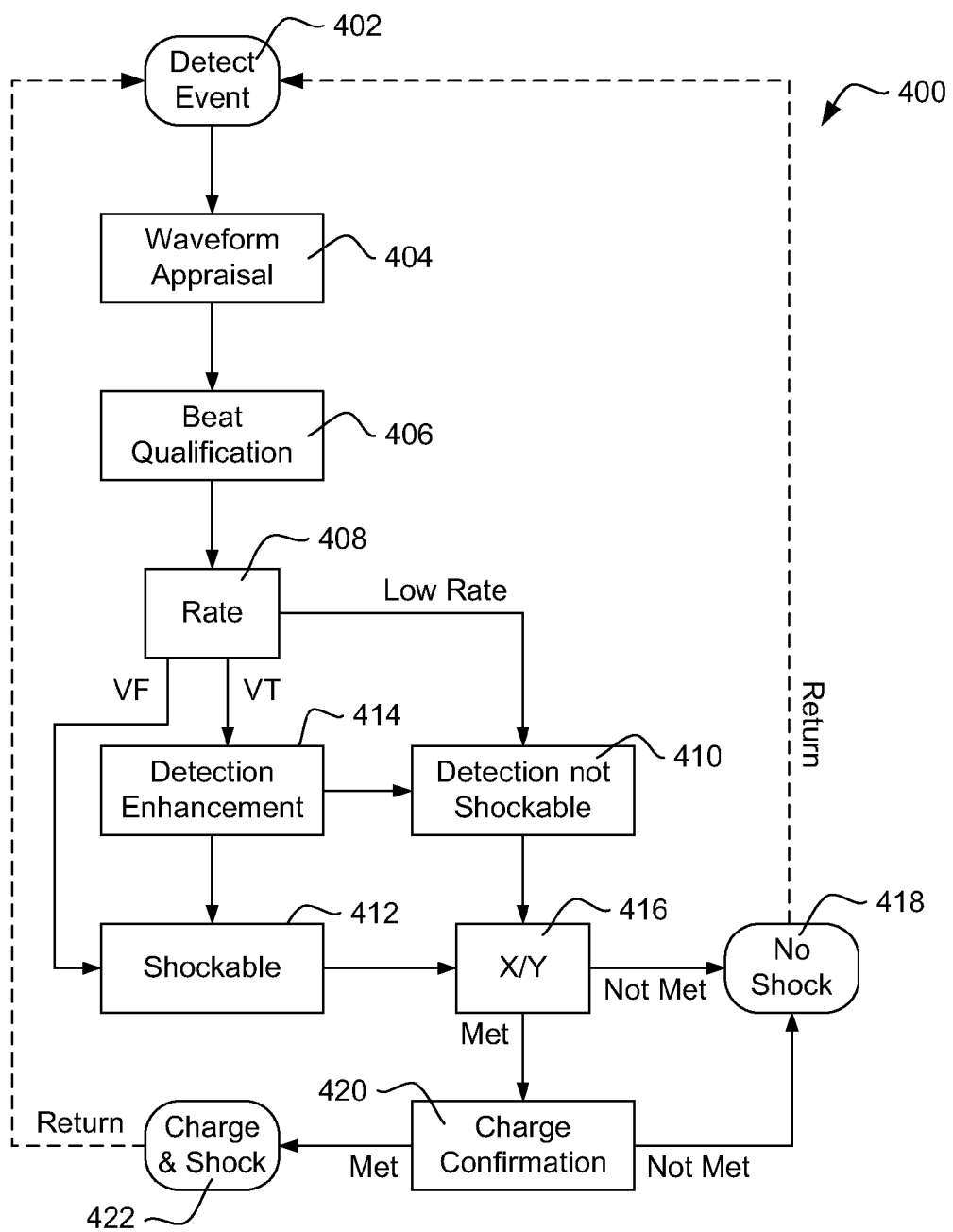
FIG. 15 shows a method of shock analysis for identifying shockable detected events and treatable rhythms.

The therapy decision 22 may include one or more of several forms of analysis. In one illustrative example, individual detected events are marked as shockable or non-shockable and an X-out-of-Y counter is maintained to determine whether the overall cardiac rhythm merits therapy. The marking of individual events as shockable or non-shockable may take several forms, including rate-based and/or morphology based determinations, or combinations thereof. FIG. 15, below, provides an illustrative example. Further examples are also discussed in U.S. Pat. No. 6,754,528, entitled APPARATUS AND METHOD OF ARRHYTHMIA DETECTION IN A SUBCUTANEOUS IMPLANTABLE CARDIOVERTER/DEFIBRILLATOR, and U.S. Pat. No. 7,330,757 entitled METHOD FOR DISCRIMINATING BETWEEN VENTRICULAR AND SUPRAVENTRICULAR ARRHYTHMIAS, the disclosures of which are incorporated herein by reference.

Therapy decision 22 may also take into account the persistence of a malignant condition. Some illustrative examples are shown in US Patent Application Publication Number 2006-0167503 titled METHOD FOR ADAPTING CHARGE INITIATION FOR AN IMPLANTABLE CARDIOVERTER-DEFIBRILLATOR, the disclosure of which is incorporated herein by reference. Other methods may be used as a part of the therapy decision 22.

Figure 2:
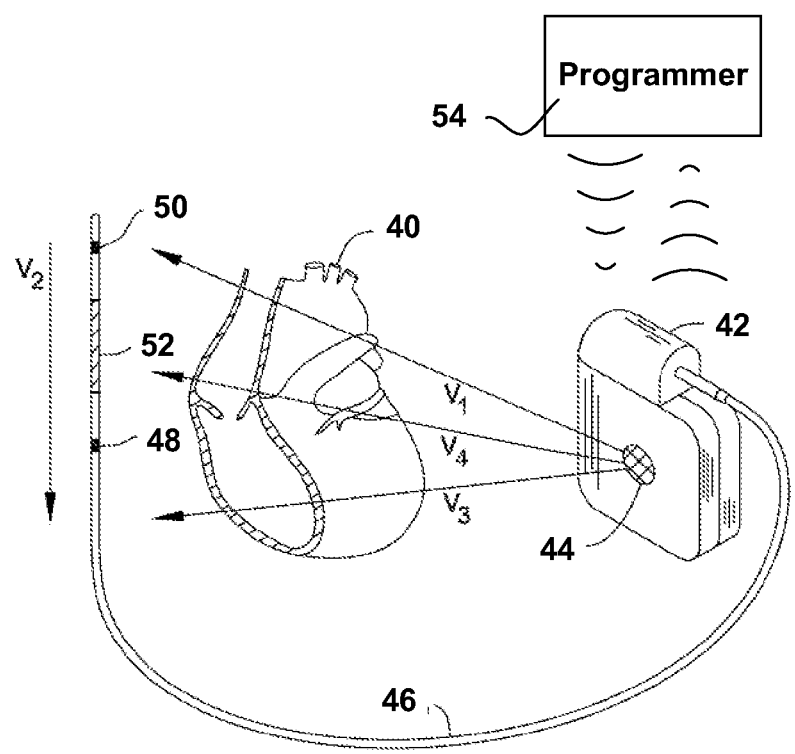
FIG. 2 shows an illustrative implantable cardiac stimulus system.

FIG. 2 shows an illustrative implantable medical device and implant location. More particularly, an illustrative subcutaneous-only system is shown in FIG. 2. The subcutaneous system is shown relative to a heart 40, and includes a canister 42 coupled to a lead 46. The canister 42 preferably houses operational circuitry for performing analysis of cardiac activity and for providing a therapy output. The operational circuitry may include batteries, input/output circuitry, power capacitors, a high-voltage charging module, a controller, memory, telemetry components, etc., as known in the art.

Electrodes are disposed at locations throughout the system including, for example, an electrode 44 on the canister 42, and electrodes 48, 50, 52 on lead 46. The electrodes 44, 48, 50, 52 may take any suitable form and can be made of any suitable material. For example, the canister electrode 44 may be an isolated button electrode or it may be a region or surface of the canister 42, and the electrodes 48, 50, 52 on lead 46 may be coil electrodes, ring electrodes, or other structures known in the art.

The electrodes 44, 48, 50, 52 define a plurality of sensing vectors such as V1, V2, V3 and V4. If desired, one or more vectors V1, V2, V3, and V4 may be chosen as a default sensing vector, for example, as discussed in US Patent Application Publication Number 2007-0276445 titled SYSTEMS AND METHODS FOR SENSING VECTOR SELECTION IN AN IMPLANTABLE MEDICAL DEVICE. Other uses of multiple vectors are shown, for example, in U.S. Pat. No. 7,392,085 titled MULTIPLE ELECTRODE VECTORS FOR IMPLANTABLE CARDIAC TREATMENT DEVICES. Another embodiment considers posture in vector analysis, for example, as discussed in US Patent Application Publication Number 2008-0188901 titled SENSING VECTOR SELECTION IN A CARDIAC STIMULUS DEVICE WITH POSTURAL ASSESSMENT. Multiple sensing vectors may be analyzed, sequentially or in combination, as desired.

Therapy may be applied using any chosen pair of electrodes. An illustrative example uses the can electrode 44 and the coil electrode 52 to apply therapy. Other electrode combinations may be used. Therapy may include monophasic or multiphasic defibrillation, cardioversion and/or pacing.

The present invention is not limited to any particular hardware, implant location or configuration. Instead, it is intended as an improvement upon any implantable cardiac therapy system. Some embodiments may also be used in a monitoring system to either control the monitoring functions (including annunciation and/or data recording) and/or to test the suitability of the data analysis to a particular configuration, condition or patient.

Some illustrative examples can associate with an external programmer 54 configured to communicate with the implanted device for various purposes, including, for example and without limitation, one or more of the following: device testing; upload new/revised software; modify programmable parameters such as detection or therapy settings; determine the status of device operation, battery life, or lead integrity; enable or disable functionality; and/or download data relating to the implantee's condition, prior data capture, or treatment. Any suitable communication method may be used, such as various protocols and hardware widely known in the art.

FIG. 2 omits several anatomical landmarks. The illustrative system shown may be implanted beneath the skin, outside of the ribcage of the implantee. The location illustratively shown would place the canister 42 at approximately the left axilla of the implantee, level with the cardiac apex, with the lead 46 extending medially toward the xiphoid and then toward the head of the implantee along the left side of the sternum. One illustrative example uses a method/system as shown in commonly assigned US Patent Application Publication Number 2006-0122676 entitled APPARATUS AND METHOD FOR SUBCUTANEOUS ELECTRODE INSERTION, now U.S. Pat. No. 7,655,014. Other illustrative subcutaneous systems and locations are shown in commonly assigned U.S. Pat. Nos. 6,647,292, 6,721,597 and 7,149,575.

The present invention may also be embodied in systems having various implant configurations including, for example, other subcutaneous-only, vascular-only, and/or transvenous implantation configurations/locations. The canister 42 may be placed in anterior, lateral, and/or posterior positions including, without limitation, axillary, pectoral, and sub-pectoral positions, as well as placements on either the left or right side of the implantee's torso and/or in the abdomen. Entirely intravascular implantation of the system has also been proposed. The canister 42 and lead 46 may be placed in any of a number of suitable configurations including anterior-posterior combinations, anterior-only combinations, transvenous placement, or other vascular placements. A unitary system may omit lead 46 and instead include all electrodes on the canister 42.

Figure 3A:
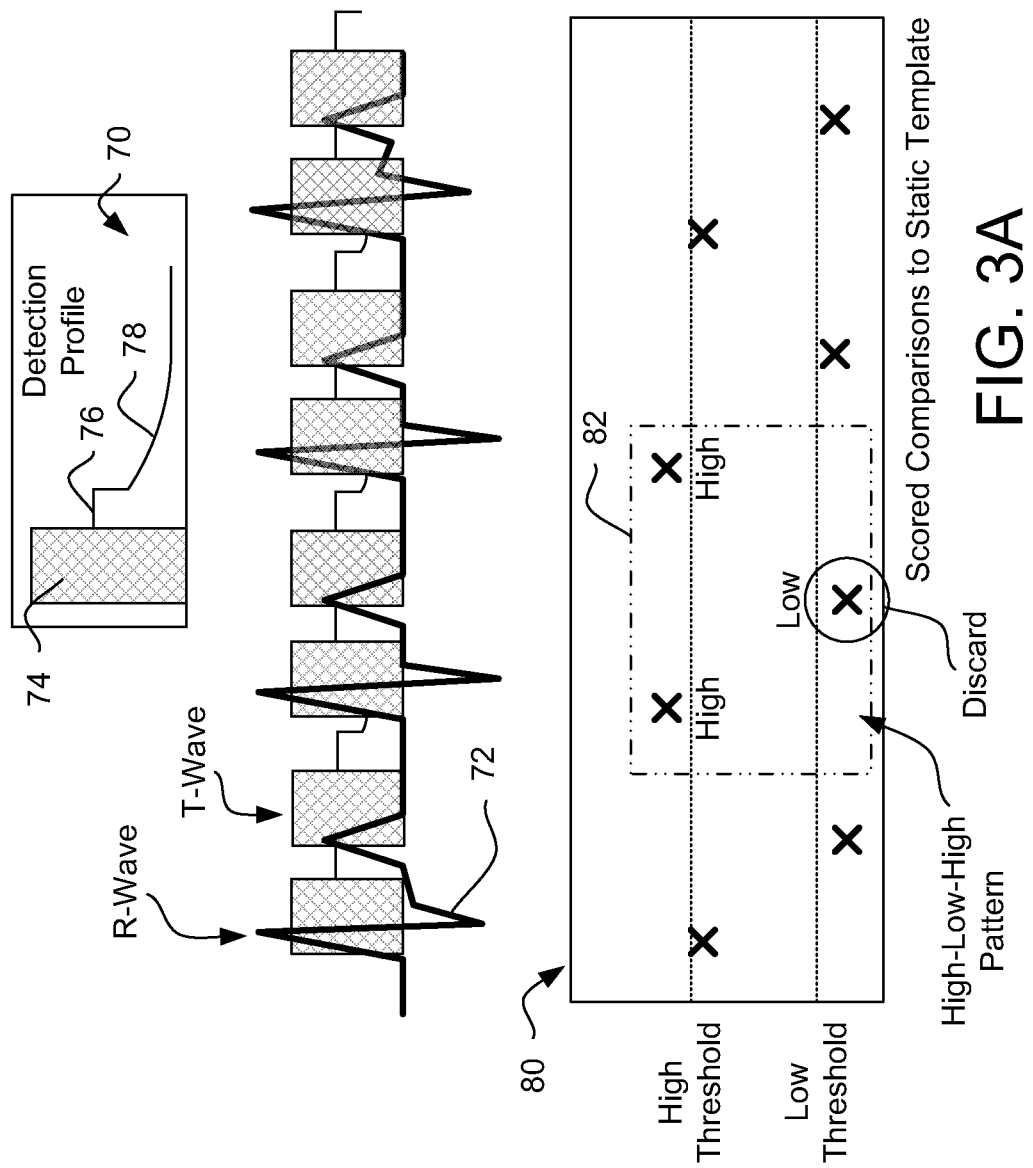
FIG. 3A shows an example using correlation analysis to identify overdetection.
Figure 16:
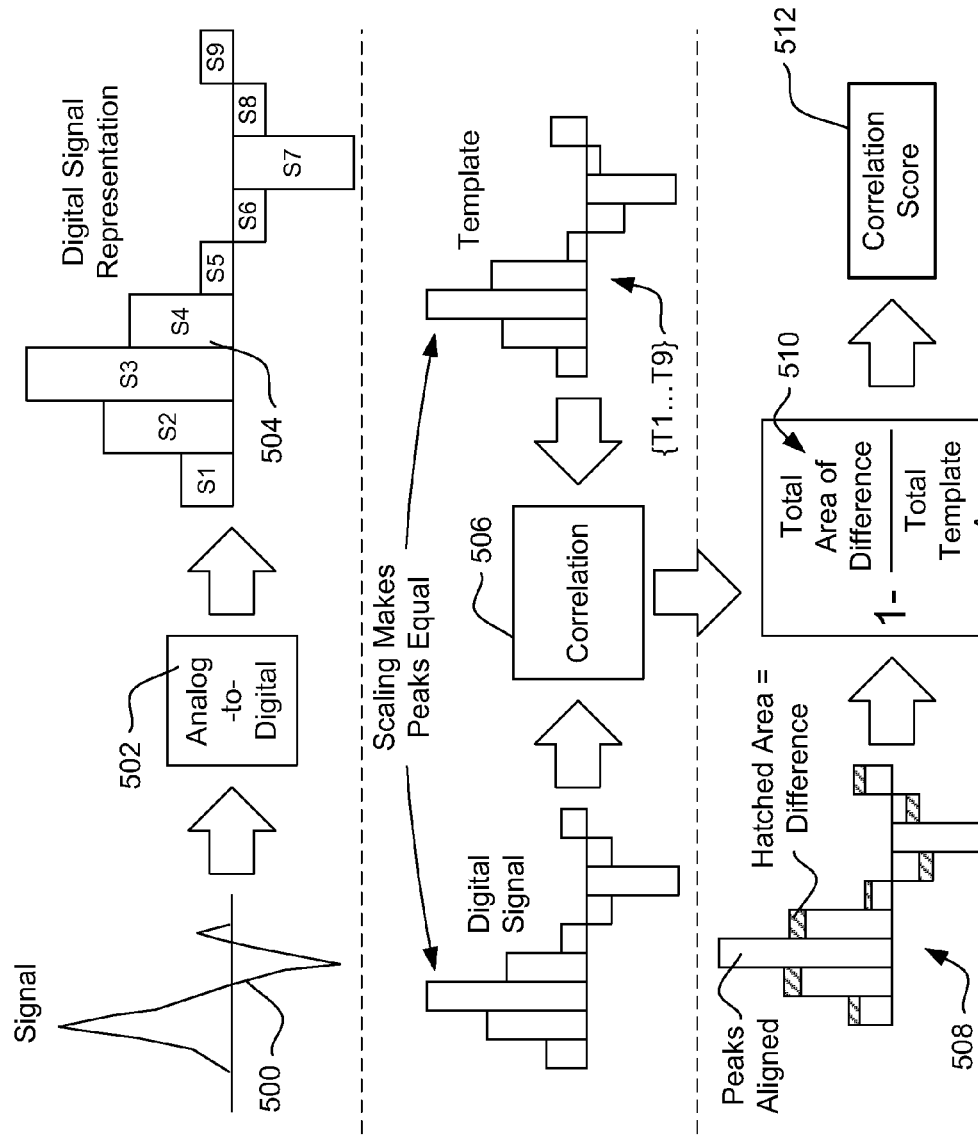
FIG. 16 illustrates a method of calculating the correlation between a captured signal and a template.

FIG. 3A shows an example using correlation analysis to identify overdetection. "Correlation analysis" as used herein can take several forms. One illustrative example is shown in FIG. 16. Referring to FIG. 16, a captured signal 500 undergoes analog-to-digital conversion 502 to yield a time ordered series of samples {S1 . . . S9} that form a sampled (and usually digital) representation of the signal, as indicated at 504. The example in FIG. 16 is simplified for illustrative purposes as the number of samples for a given signal may be greater than nine. For example, in one illustrative embodiment, the captured signal 500 is about 160 milliseconds long, covering 41 samples captured at 256 Hz. Other durations and/or sampling frequencies may be selected. The signal can be windowed to approximately the QRS width, though this is not required.

The signal representation is compared to a template using correlation analysis 506. The template is shown as comprising a series of sample values {T1 . . . T9}. Prior to comparison, or as part of the comparison, the signal representation or template is scaled such that the largest peaks of the two data sets are equal in amplitude. One example of correlation analysis is correlation waveform analysis. Other examples are widely known in the art.

A simple version of correlation analysis is shown graphically in FIG. 16: the largest sample or peak of the signal representation is aligned with the peak of the template and the surrounding samples are compared to one another as shown at 508. Because the peaks are already scaled to be equal, there is no difference at the peak, but the surrounding samples may differ. Differences between the signal representation and the template are shown in cross-hatching.

Next a correlation score may be calculated as shown at 510. The sum of the absolute values of the differences between (scaled) samples of the signal representation and samples of the template is calculated and divided by the total area under the template. The quotient is subtracted from one, yielding a correlation score 512. If the correlation score is close to one, then the area of difference is small relative to the area under the template, indicating high correlation. Other methods for calculating correlation are known in the art and may be substituted; that shown in FIG. 16 is simply an example. For example, a weighted CWA may apply a weighting factor to individual sample differences in a fashion as shown in commonly assigned, copending US Patent Application Publication Number 2008-0077030, which is now U.S. Pat. No. 8,014,851.

Returning to FIG. 3A, individual events are detected by applying a detection profile 70 to a signal 72. The detection profile 70 includes a refractory period 74 followed by a constant threshold period 76 and a decay period 78. Other shapes may be used for the detection profile 70.

The signal 72 has R-waves and T-waves highlighted. In the example shown, the T-waves are large relative to the R-waves. The refractory periods shown in cross-hatching over both R-waves and T-waves indicates that each R-wave and each T-wave is being treated as a detected event. As a result, for each cardiac cycle, the detection profile 70 is detecting two events. This is one example of overdetection.

In the illustrative example, each of the individual detections is also being treated to correlation analysis relative to a template that is based on an R-wave. The results of the correlation analysis are plotted at 80. Plot 80 includes boundaries for "High" and "Low" correlation. In the example, each "X" indicates the correlation score for each detected event. A High-Low-High pattern of correlation scores occurs as shown at 82. In the example, each High-Low-High sequence leads to a conclusion that "Low" scoring detected events are overdetected. As a result, as shown, the "Low" scoring detected event will be discarded when a High-Low-High pattern is found. In a numeric example, "High" is defined as greater than 52% correlation, while "Low" is defined as less than 25% correlation, when calculated using the form shown at 510 in FIG. 16. Other values and analytical methods can be used.

Figure 3B:
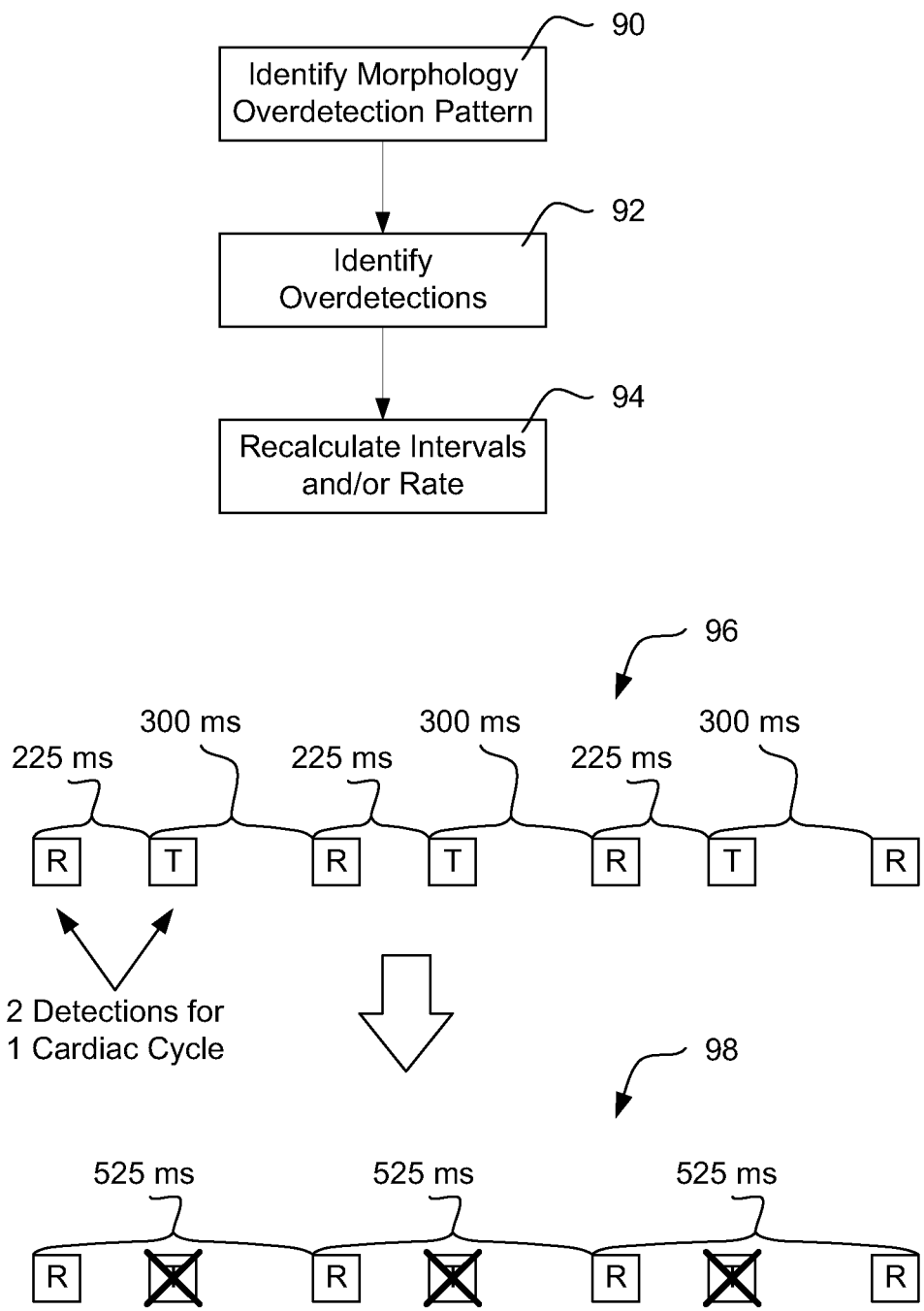
FIG. 3B illustrates method steps for an illustrative example including rate correction.

FIG. 3B illustrates method steps for an illustrative example including rate correction. Once a morphology overdetection pattern is found, as indicated at 90, one or more overdetections are identified, as shown at 92. Next, event intervals and/or rate are recalculated, as shown at 94.

For example, as shown at 96, a series of detections of R and T waves may result in a set of interval calculations of 225 ms (R to T) and 300 ms (T to R), which yields an average interval of 263 ms. An average interval of 263 milliseconds leads to a rate of about 229 beats-per-minute, which would be a treatable tachyarrhythmia in many patients. However, when the T-waves are identified as overdetections and the intervals on either side of the T-waves are combined, as shown at 98, the intervals average 525 milliseconds. The rate can be recalculated to about 114 beats-per-minute, avoiding possible defibrillation, cardioversion or pacing that could result without the data correction.

FIG. 4 shows an example of inter-event correlation comparisons. An inter-event comparison is a comparison in which two individual detected events are compared to one another. The comparison may take the form of a correlation analysis, or it may make use of some other type of analysis such as wavelet transform, principal component analysis (PCA), etc., to consider the similarity between two detected events. In wavelet transform or PCA comparisons, the similarity of the results of data compression into wavelet or PCA outputs can be compared. For example, the similarity and/or order of eigenvalue outputs of PCA, or the similarity of the wavelet coefficients resulting from a wavelet transformation can be compared in a qualitative or quantitative manner.

In the example shown in FIG. 4, a correlation analysis is performed. In the example, as shown at 108, correlation scores are characterized as Low, Middle, or High. The "High" score zone indicates strong confidence that the compared signals are of the same character (for example, if one event is an R-wave, so is the other), while "Low" scores indicate that the compared signals are very different from one another. The "Middle" zone is intended to capture those signals that are similar but that do not create strong confidence that the two signals are of the same character. For example, in a patient who undergoes a rate-dependent morphology change (such as a rate-induced bundle block), captured R-waves may not highly correlate to a stored static template but likely fall into the Middle range relative to the template. In another example, a monomorphic VT likely has High or Middle inter-event correlation between R-waves, and Middle correlation between T-waves, while a polymorphic VT would show Middle or Low correlation between R-waves.

If desired, fuzzy logic may be applied. The use of a "Middle Zone" suggests this. For example, rather than simple "High" and "Low" characterizations, additional categories may be provided. Further, a previous measurement may be used to inform a subsequent characterization of a marginally similar or dissimilar signal.

As shown at 100, a series of events N, N−1, N−2 and N−3 are considered as a group, with the $N^{th}$ detection compared to each of N−1, N−2 and N−3 via correlation analysis. The results of inter-event comparisons and comparisons to a static template are shown in a table at 102. The inter-event comparison results are shown at 104, and include ordered results for comparison of a given event to three prior events. Table 102 shows results for events N, N−1, N−2 and N−3. The results of the inter-event comparisons show that for any given event X, the correlation to X−2 is higher than for X−1 or X−3. This may indicate a pattern of double detection based on increased correlation between alternating events.

In the illustrative example, comparisons to a static, normal sinus rhythm template may be performed as well. Illustrative results are shown at 106. The alternating static template results, Low-Middle-Low-Middle . . . are suggestive of possible overdetection, but because the likely R-waves do not Highly correlate, strong confidence does not result based on static template alone. However, when taken in combination with the inter-event comparison information, there is significant confidence that some events are overdetections. An applicable rule set may be as follows:

1) Alternating Low-High-Low for N when compared to N−1, N−2 and N−3, and
2) Alternating Low-High-Low for N−2 when compared to N−3, N−4 and N−5.

Conclusion: Treat N−1 and N−3 as T-waves.
A further, confirmatory rule may be:
3) At least "Medium" correlation for N and N−2 to static template.

Another approach is to apply only rules 1) and 3), while marking only the N−1 as an overdetection in response to the rule set being met. Once one or more events are marked as overdetections, they may be treated in the manner shown in FIG. 3B, above.

Figure 5:
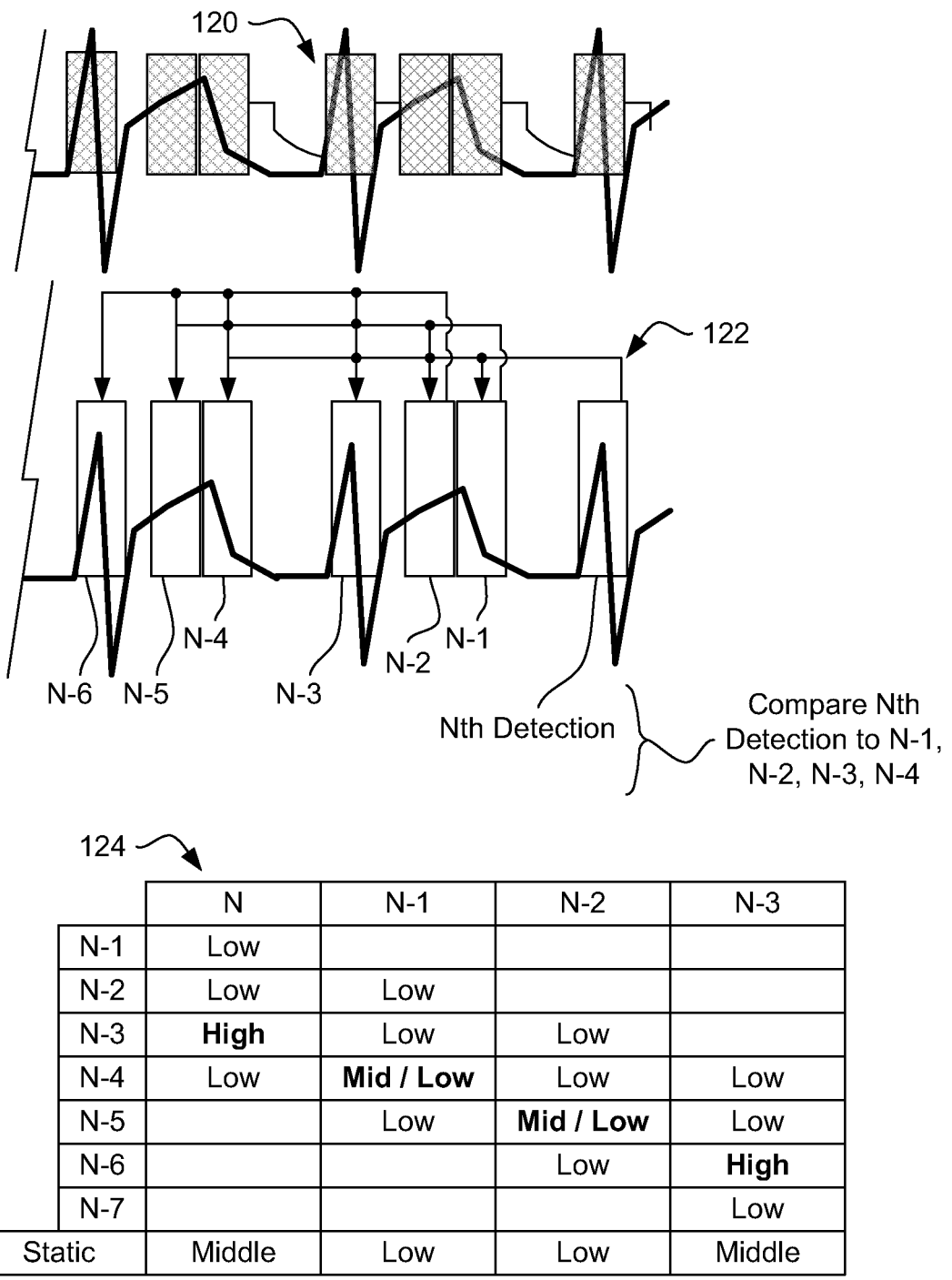
FIG. 5 shows another example of inter-event correlation comparisons.

FIG. 5 shows another example of inter-event correlation comparisons. Here the captured signal is triple-detected, as shown at 120. In this instance, the Nth detection is compared to each of N−1, N−2, N−3 and N−4. The inclusion of four individual comparisons may further assist in distinguishing a triple detection from a double detection, although some embodiments stop at three comparisons.

The results are shown in the table at 124. For each set of comparisons, there are three Low correlations, and one Middle or one High correlation. It is likely that with triple detection, some detections will have a low correlation in each comparison. An illustrative rule set is as follows:

1. Nth event has High correlation to the N−3 event;
2. N−1 and N−2 events have Low correlations to the Nth event; and
3. N−1 and N−2 events have Low correlations to the Static Template.

If these three conditions are met, then N−1 and N−2 may be discarded. Further conditions may be added. For example, the static template characteristics of N and/or N−3 may be considered as well, for example:

4. Nth and N−3 events have Middle or High Correlation to Static Template. Then if all of 1-4 are met, N−1 and N−2 may be discarded and the interval from N to N−3 calculated and used in rate analysis.

In a further example, the widths of each event may also be considered, for example using this fourth condition:

5. N−1 and N−2 events are wider than a Width Threshold. The width threshold may be set as desired; in one example the Width Threshold is in the range of 100-140 ms. This Width Threshold rule may be applied as an added layer to any determination that an event is to be discarded as an overdetection. In another example, the polarities may be considered:

6. N–1 and N–2 each share the same polarity.

Polarity may be defined, for example, by reference to the majority of signal samples for an event, as the polarity of the sample having the greatest magnitude in the event, or by determination of which extreme, the most positive or least positive, in the event occurs first.

If desired, interval coupling may be added as another condition:

7. The combined interval N to N–3 less than Duration.

Where "Duration" is in the range of 800-1200 ms. This condition, and variants thereof, is also explained in association with FIGS. 11-13 and 14A-B below.

FIG. 6 shows an analytical approach to short series and long series correlation analysis. FIG. 6 shows a plot 140 for plotting the correlation scores for a series of detected events. The correlation scores, shown as X's, are plotted against lines 144 and 146 that define a wide band 148, and lines 150, 152 that define a narrow band 154.

The wide band 148 is applied to identify an overdetection when there are two detected events with scores above line 144 separated by a single detected event with a score below line 146, for example as shown in FIG. 7A. The narrow band is applied to identify overdetection(s) when a series of consecutive detections alternate above line 150 and below line 152, for example as shown in FIG. 7B. Numbers are shown for each threshold for illustrative purposes; these numbers may use correlation as a percentage.

The narrower band 154 applies a less stringent standard than the wider band 152 with regard to the correlation scores, and therefore more events are analyzed before making a decision to discard low scoring events. In one illustrative example, events are not discarded using the narrow band 154 until the 8 event pattern shown in FIG. 7B is met, at which point one to four of the low scoring events are discarded, with intervals around each discarded event being corrected. Subsequent to meeting the pattern in this initial step, only the newest low scoring event would be discarded. For analytical purposes, previously discarded events are used to determine whether the 8-consecutive-outside rule is met, even if those events are excluded from rate calculations. Another embodiment uses only five events, looking for a High-Low-High-Low-High sequence using the narrower band 154 and, if such a sequence is found, one or both of the Low scoring events is discarded.

The examples in FIGS. 6 and 7A-7B indicate numbers, with 50% and 20% correlations bordering the wide band 148 and 40% and 25% bordering the narrow band 154. These numbers are merely illustrative. In one example, these numbers are applied by scaling the formula shown at 510 in FIG. 16 to a percentage basis.

FIGS. 8A-8B illustrate examples of tailoring correlation analysis to observed levels of correlation to a template. Referring to FIG. 8A, a plot of correlation scores for comparing a template to a series of events is shown at 158. For purposes of identifying double detections, a mean correlation score is calculated for the odd numbered events. Clustering of the odd numbered events is then analyzed by determining whether the odd numbered events all fall within a predefined distance from the mean, for example, using the standard deviation of the set, or using a fixed distance. If the odd numbered events all fall within the predefined distance from the mean, the separation of the mean from a Low boundary is calculated. If the separation is greater than a predetermined threshold, then it is determined that the odd numbered events demonstrate monotonicity supporting a presumption that the odd numbered events are QRS complex detections. If monotonicity of the odd numbered events is identified, one or more of the even numbered events that fall below the low threshold are marked as overdetections.

In another embodiment, before any of the even numbered events are marked as overdetections, they are all analyzed to determine whether clustering of the even numbered events has taken place, again using the mean of those events. Rather than separation of the odd-numbered event mean from a low boundary, separation between the even and odd event means is calculated to establish groupings of the events. In this embodiment, overdetection markers are applied only when sufficient clustering of the even-numbered events appears.

FIG. 8B shows another example in which the marking of overdetections is tailored to correlation scores to a static template. Here, the average correlation score for a set of 10 events is calculated. A "blank" band is then established around the average correlation score. For example, the blank band may be defined as +/–15%. Other "blank band" sizes may be used.

In the example of FIG. 8B, high scores are defined as those scores that fall above the blank band, and low scores are those falling below the blank band. If a pattern of High-Low-High appears around the blank band, then overdetection can be identified and one or more of the Low scoring events is marked as an overdetection.

Instead of a static template, the analysis shown by FIGS. 8A-8B may also be applied using a recently detected event as the template for comparison. The analysis noted for FIGS. 8A-8B may use calculation of the mean/average, or it may use some other predictor of a center-point for signals including the mode, median or other mathematical operation.

A further use of the inter-event comparisons shown here may be in the determination of whether a Shockable rhythm is occurring. Stimulus delivery is often used to address polymorphic conditions, such as Polymorphic Ventricular Tachycardia and Ventricular Fibrillation. Monomorphic conditions such as Monomorphic Ventricular Tachycardia (MVT) can be treated, but MVT does not always require the most energetic treatments. For example, MVT may be treated using anti-tachycardia pacing (ATP) in place of defibrillation or cardioversion, as ATP uses less energy and may be less traumatic to the patient. Patterns of correlation can be used to distinguish monomorphic arrhythmias from polymorphic arrhythmias. For example, an ongoing pattern as shown in FIG. 7A or 7B, or even FIG. 6, in which high correlations are consistently found, can be used to delay therapy, if desired.

In another example, a pattern as shown in FIG. 8A may be further analyzed by determining the size of the standard deviation for the clustered high scores. If the clustered high scores are based on a static template and show a low standard deviation, this may indicate a monomorphic condition. In some embodiments, particularly if ATP is not available, therapy may be inhibited until the monomorphic condition breaks down into a more polymorphic condition.

In one example, a system uses a tiered correlation analysis to identify treatable arrhythmias. In the example, a simple, single event correlation analysis using a static template is executed until a pattern as shown in FIG. 8A appears. Such a pattern then triggers multiple inter-event comparisons as shown in FIGS. 4-5. Then, if the inter-event comparisons show likely overdetection, interval data may be corrected. Further, if inter-event comparisons show a monomorphic condition, therapy may be inhibited.

Figure 9:
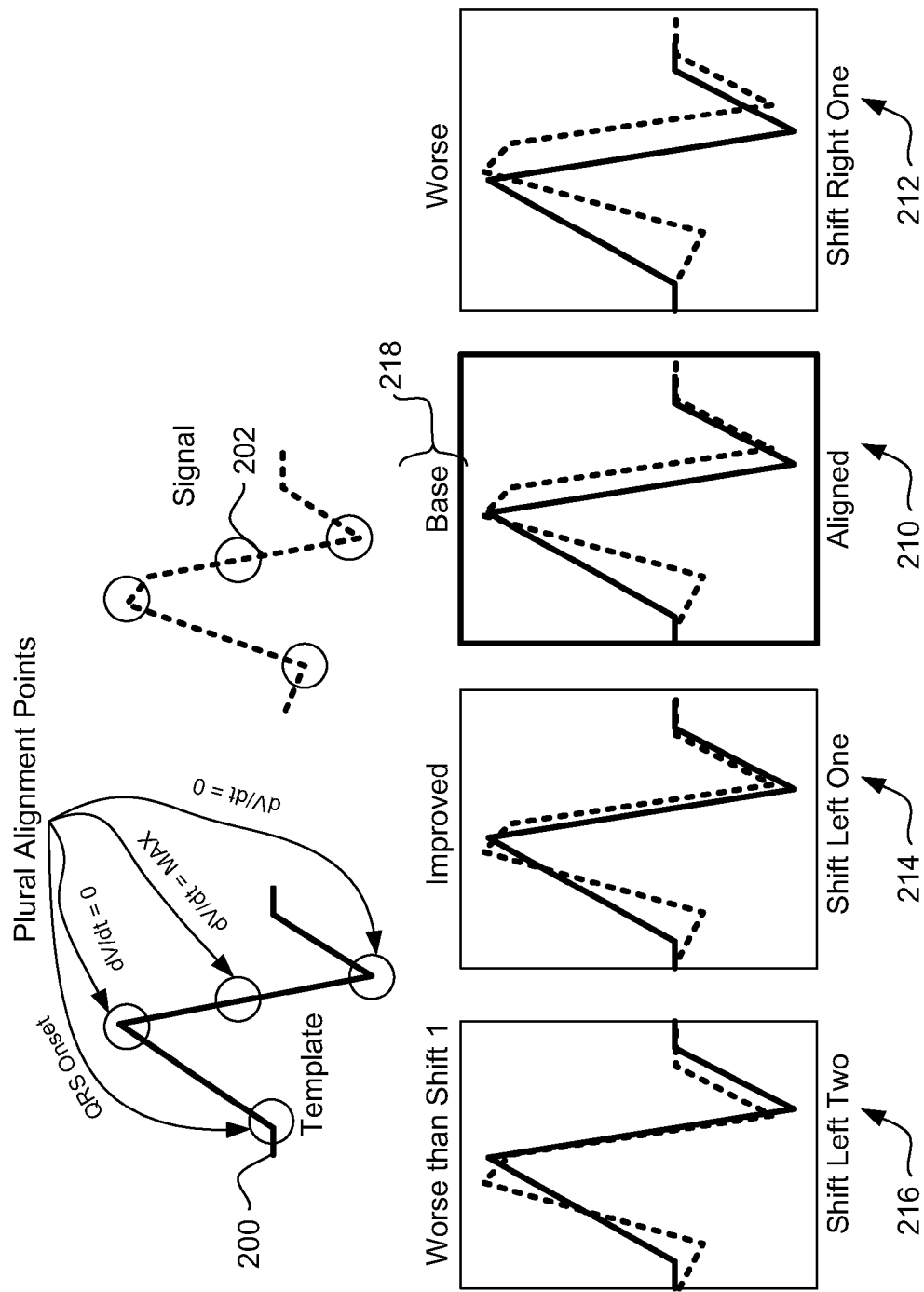
FIG. 9 illustrates another method of aligning captured signal to correlation analysis templates.

FIG. 9 illustrates methods for aligning and realigning a captured signal to a correlation analysis template. The correlation analysis template is shown at 200, with a signal shown at 202. The correlation analysis template 200 may be a static template or it may represent a single detected event or average of several recently detected events.

As noted in FIG. 16, correlation analysis typically uses a fiducial point as an alignment guide for an ordered series of template values and signal samples. In the example of FIG. 9, a base alignment point is identified as the sample of each of the template 200 and the signal 202 having the greatest magnitude. A series of comparisons are then made, beginning with a base aligned comparison, shown at 210, and single-sample shifts to the right, shown at 212, and the left, shown at 214. The shift one right correlation 212 is worse than the correlation score for the base comparison 210, and so the result of the shift one right correlation 212 is discarded. The shift one left correlation 214 yields a higher correlation score than the aligned correlation 210, so the result of the base correlation 210 is discarded, and another shift left correlation is calculated as shown at 216, this time offsetting the alignment points by two samples. The result at 216 shows lesser correlation than the shift-one-left correlation at 214, and so the process stops and uses the correlation score calculated for the shift-one-left correlation 214 as the correlation score for the signal 202.

When performing the shifting to the right and/or left, scaling of the signal to the template may be modified as well. For example, if scaling is initially performed by comparing the peak for the signal to the peak for the template and then equalizing the two, on shifting, the peak for the signal may instead be scaled to the point it aligns to in the template after shifting has occurred.

The method demonstrated in FIG. 9 may help to correct for noise or misalignment based on sampling artifact, slew rate, etc., that may cause the peak alignment point of the sample 202 to be less than optimal. The method includes calculating the correlation score when the fiducial points are aligned and also when the fiducial points are misaligned by one or more samples in each of two directions until a maximum correlation score is found. Limits may be placed, as desired, on the number of samples to shift to the left or right. In another embodiment, several (for example, one base, one, two, and three to the left, one, two and three to the right) scores are automatically calculated and the best is chosen.

In another embodiment highlighted in FIG. 9, plural alignment points can be defined for the template 200. Some examples include the QRS onset, the maximum amplitude, the maximum amplitude in the opposite polarity of the maximum amplitude (note the maximum amplitudes are indicated by each being a turning point where dV/dt=0), the maximum slope point between the two major peaks (shown as dV/dt=MAX, etc.). By identifying the analogous points in the signal, the method can determine whether use of different possible alignment points would provide different correlation analysis outcomes. For example, the default may be to use the maximum amplitude point of the entire signal, but it may be that some cardiac events can be aligned instead using the maximum slope point in the monotonic segment that follows the maximum amplitude point.

Figure 10:
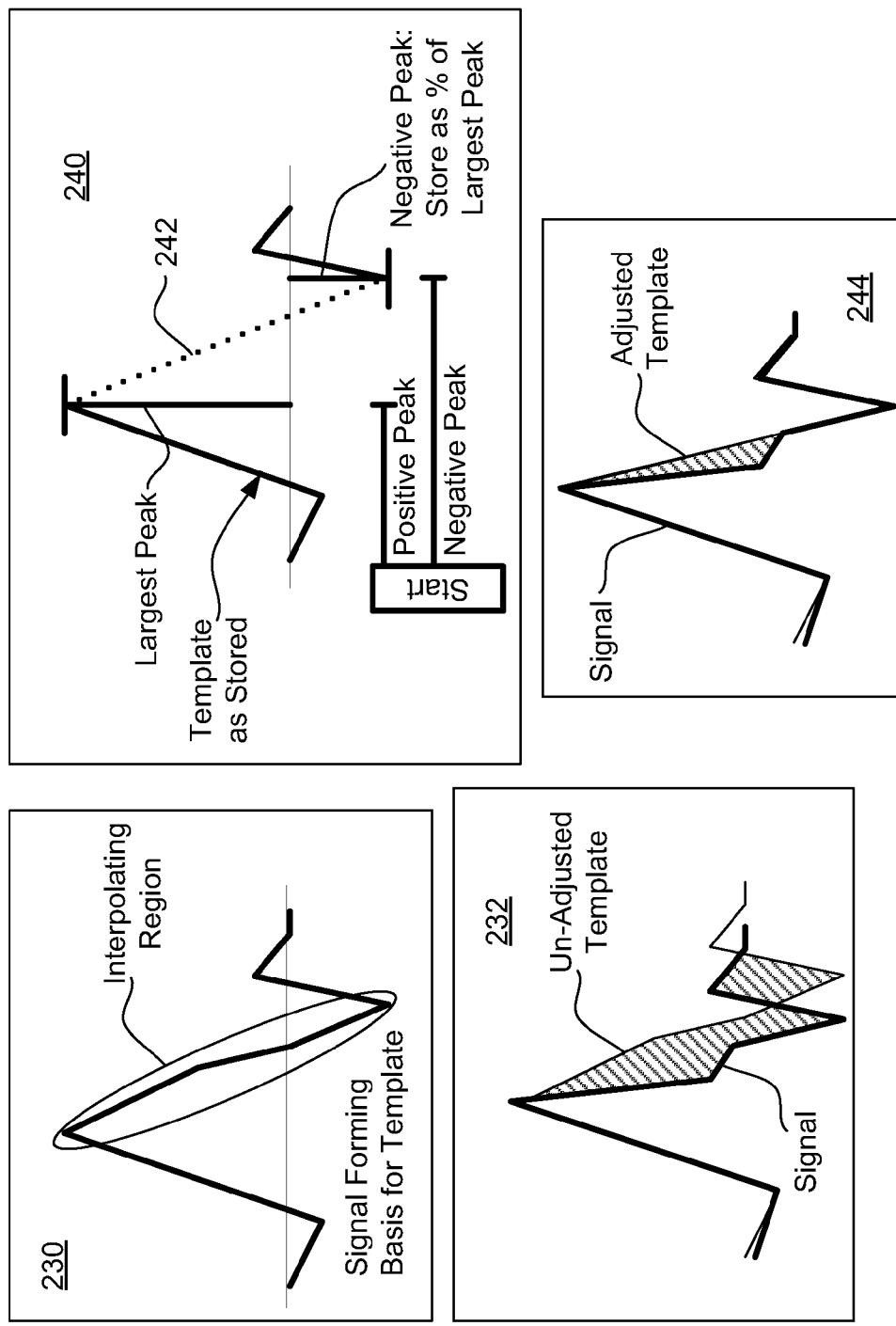
FIG. 10 shows another method of storing and applying a template for correlation analysis.

FIG. 10 shows another method of storing and applying a template for correlation analysis. In this example, the signal forming a basis for a template is shown at 230. For the illustrative example, when the template is formed an interpolation region is defined between the positive peak and the negative peak of the signal 230. As a result, the stored template takes the form shown at 240: The template 240 matches the template signal 230 for regions before the positive peak and after the negative peak, but is flexible between the two peaks, as indicated by the dashed line at 242. The positive peak, in the example shown, is the largest magnitude peak in the template, and so it is used for scaling the template to a captured signal.

Alignment to a sample 232 is then performed as shown at 244. The template is adjusted such that the positive and negative peaks are aligned with the captured signal, with a linear interpolation therebetween. Outside of the positive and negative peaks, the template continues to match the signal as shown at 230, however, the duration and slope between the positive and negative peaks are adjusted to match the captured event. The adjustment shown in FIG. 10 may avoid the difficulty of a static template being fixed in duration for a patient whose QRS width is affected by rate. The adjustment made may be limited in order to avoid excessively widening the template.

In another example, more than two template points are identified and linear interpolation may be used between them. For example, a template may be composed of five values each having a relative amplitude and relative location. When a detected event is to be compared to the template, the width and peak amplitude of the detected event are used to scale each of the values of the template, with linear interpolation between the template points.

Figure 11:
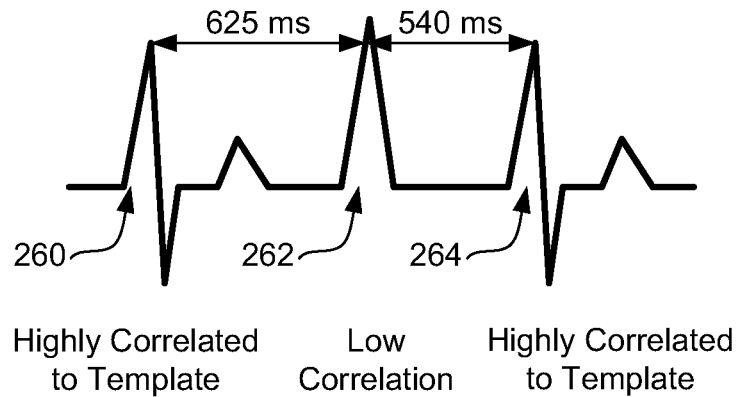
FIGS. 11-12 illustrate a method of inhibiting correlation analysis identification of an overdetection.
Figure 12:
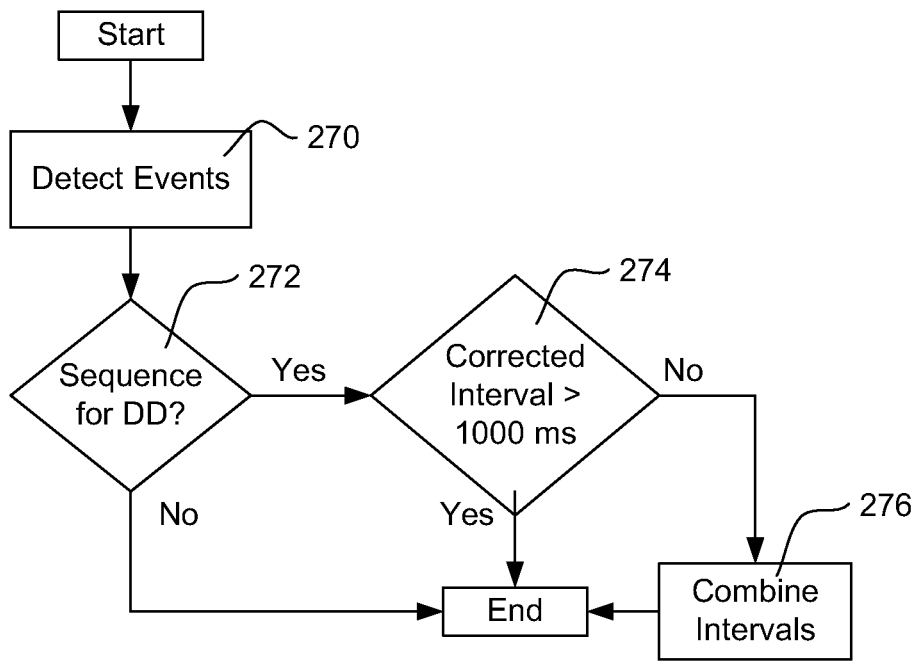

FIGS. 11-12 illustrate a method of inhibiting data correction following identification of a likely overdetection.

As shown in FIG. 11, a QRS complex occurs at 260, followed by a premature ventricular contraction (PVC) shown at 262, following by another QRS complex at 264. The PVC is characterized, in this example, by a low correlation to the template. Thus, a High-Low-High correlation pattern appears, similar to that shown above in FIG. 3A. Some examples would therefore discard the PVC 262. Analytically, however, discarding the PVC 262 may be unnecessary since it is not actually an overdetected event. Further, the intervals around the PVC 262 are both greater than 500 milliseconds. Even without data correction, the average of the two intervals would yield an event rate of about 103 beats-per-minute, a rate that would not threaten to cause unnecessary therapy. Thus the data correction would not improve rhythm specificity in the device, while reducing beat sensitivity.

FIG. 12 illustrates a method that would avoid discarding a PVC 262 as shown in FIG. 11. Based on detected events 270, the method determines, as shown at 272, whether a correlation score sequence appears that would support a finding of double detection (DD) or overdetection. If not, the method ends, as no data correction is about to ensue. If the result from 272 is a "Yes," the method next includes determining whether the new interval that would result from data correction would be greater than a predetermined threshold, as shown at 274. In the illustrative example, the threshold is 1000 ms (60-beats-per-minute), though this number is merely illustrative. Some likely thresholds are in the range of 750-1200 milliseconds.

In another example, the order of analysis is reversed, and the overdetection analysis does not take place unless the calculated rate is high (often 150 bpm or more), or unless the intervals that could be affected are short enough to pass the applied test. In another embodiment, individual intervals are compared to a threshold (for example, in the range of 400-600 ms) and, if the individual intervals both exceed the threshold, then no interval combining occurs. In yet another example, the threshold may be a programmable parameter of an implantable system. In another example, the threshold may be scaled on the basis of a programmable VT parameter that is used to set a beat rate that the implantable system will treat as a ventricular tachycardia rate.

If the corrected interval is not longer than the threshold, the method continues to the step of combining intervals, as shown at 276, to correct for the overdetected event(s). If the corrected interval would be longer than the threshold at step 274, the method simply ends without combining intervals. In this fashion, unnecessary correction of the stored data can be avoided.

Figure 13:
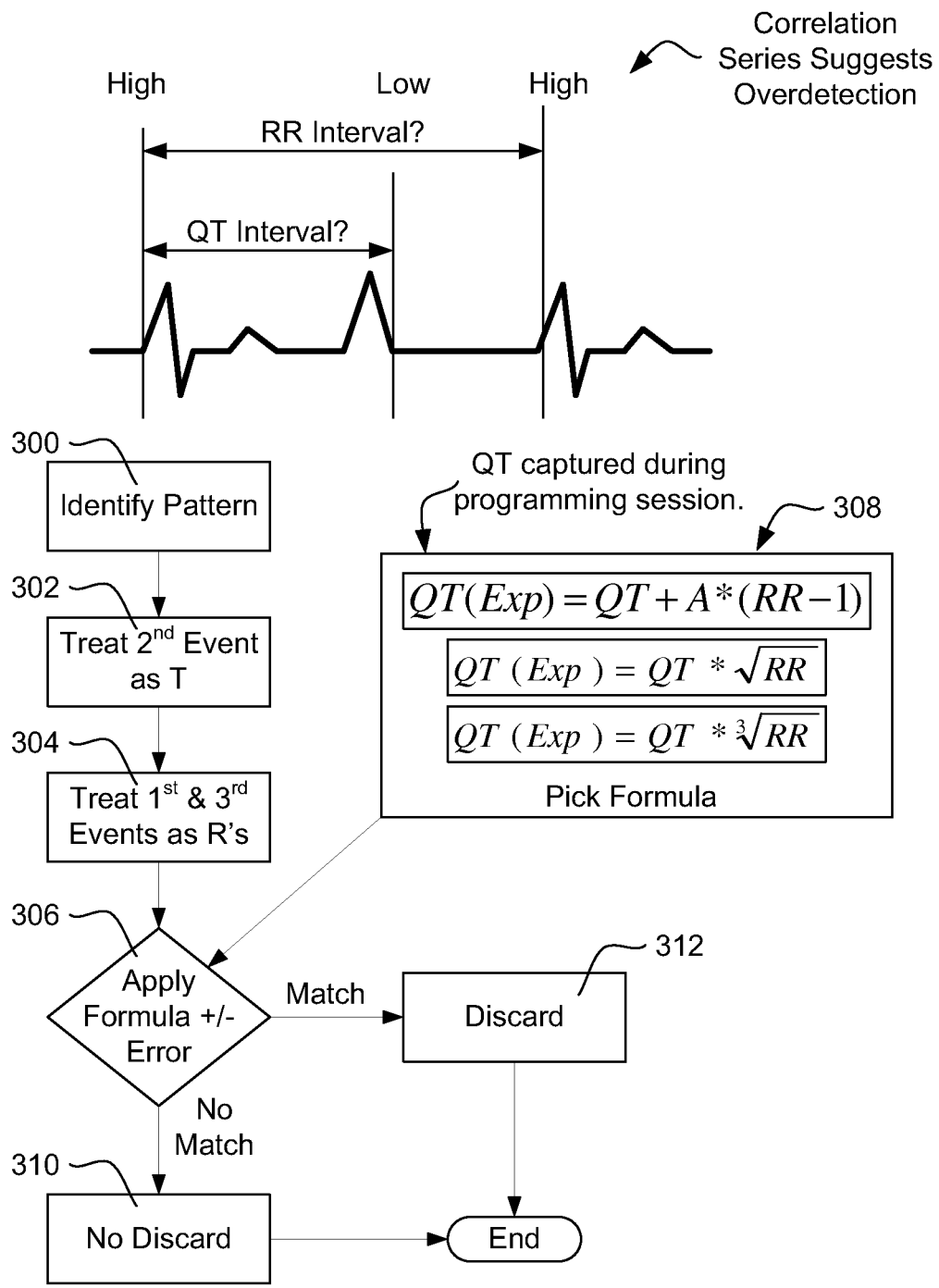
FIG. 13 illustrates more methods for inhibiting correlation analysis identification of an overdetection.

FIG. 13 illustrates more methods for inhibiting correlation analysis after identification of an overdetection. The methods in FIG. 13 take advantage of known relationships between the QT interval and the RR interval of physiologic cardiac cycles. The illustrative method again begins with the identification of a pattern that suggests overdetection, as indicated at 300. As shown at 302, the possible overdetected event is then treated as a T-wave (here, the presumption is that a three-event pattern is identified, with the middle event of the three being the likely overdetection; other variants may be used) and, as shown at 304, the events on either side of the likely overdetection are treated as R-waves.

These "presumed" R and T waves from steps 302 and 304 are then used to apply a formula for calculating the QT length from the RR interval in step 306. In particular, several likely formulae are shown at 308. Examples include Bazett's formula:

$$QT(\text{Exp})=QT*\sqrt{RR}$$

Friderica's formula:

$$QT(\text{Exp})=QT*\sqrt[3]{RR}$$

And the Sagie et al. regression formula:

$$QT(\text{Exp})=QT+A*(RR-1)$$

Sagie et al. found A=0.154.

In each formula, the expected QT is shown as QT(exp), the value RR is given in seconds, and the value QT is captured during a programming session between an implant and a programmer. QT is either captured at or adjusted for a 60 beat-per-minute cardiac rate. The RR interval is found at step 304, and the measured QT interval can be captured by adding the measured width of the presumed T-wave to the interval between the first R-wave and the presumed T-wave.

The expectation is that if the likely overdetected event is an overdetected T-wave, the measured QT period will match the expected QT value given RR, using whichever formula is applied, with some band allowing for error.

If the formula applied at 306 does not yield a match, no discard occurs, as shown at 310. Alternatively, if the formula applied at 306 yields a match, then the likely overdetection is discarded as shown at 312. When the likely overdetection is discarded at 312, intervals around the overdetection are combined, as shown above in FIG. 3B. Once again, the order of analysis is reversed in other examples.

Figure 14A:
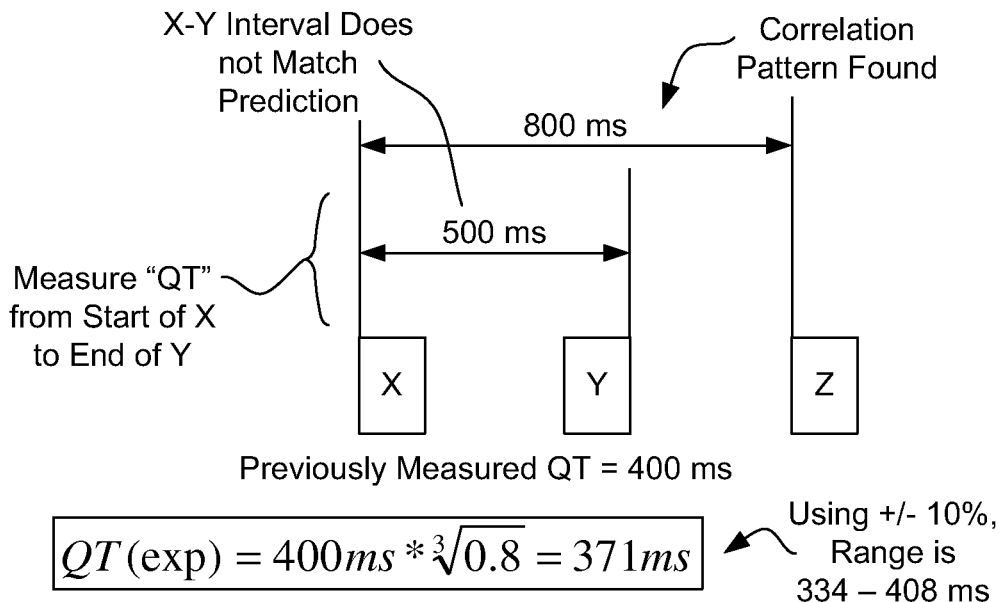
FIGS. 14A-14B show application of a method illustrated in FIG. 13.
Figure 14B:
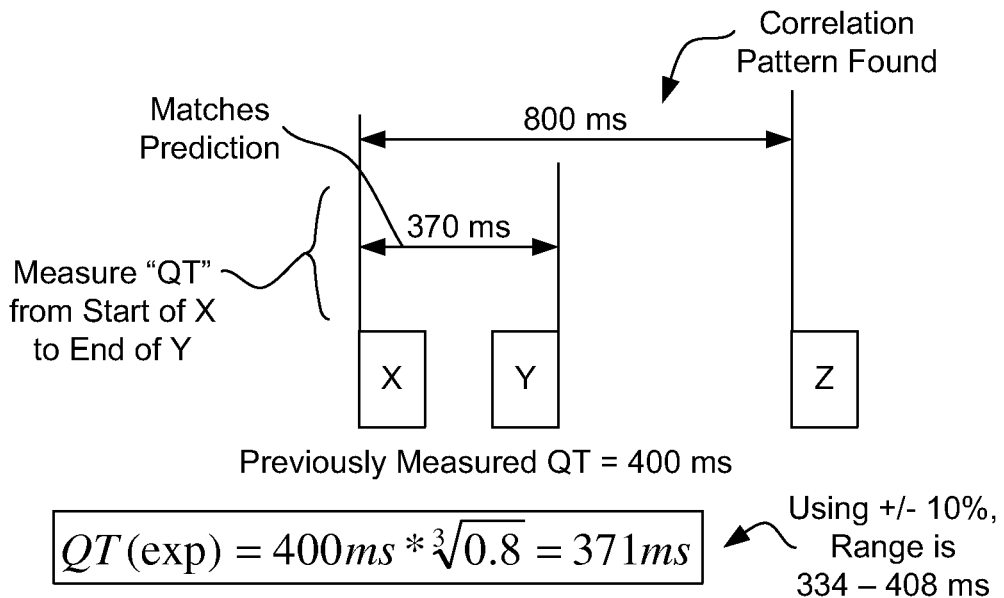

FIGS. 14A-14B show application of a method illustrated in FIG. 13. In the illustrative examples of FIGS. 14A and 14B, Friderica's cube-root formula is applied. In each example, the previously measured QT=400 milliseconds. This value represents the estimated QT interval for the hypothetical patient that would occur at a heart rate of 60 bpm.

Referring to FIG. 14A, given three events X, Y and Z having a correlation pattern indicating overdetection, the method is applied by presuming that Y is a T-wave. The QT interval is measured for X and Y, and the RR interval is measured from X to Z, as indicated. The measured QT is referenced as well, and these values are plugged into the chosen formula. In the example, shown, using RR=0.8 seconds, the expected value for QT is 371 milliseconds. Applying a +/−10% error band for the calculation, the acceptable range is about 334-408 milliseconds for QT. However, as shown, the measured interval is about 500 milliseconds, too long to be a QT interval for the given parameters. As a result, the calculation suggests that the Y detection is not an overdetected T-wave, and therefore no data correction occurs. Lesser or greater error band sizes may be applied; for example, +/−5% error is used in another illustrative embodiment.

Referring instead to FIG. 14B, this time, the QT interval measured for X and Y is about 370 milliseconds. This value falls within the expected range, and therefore the calculation suggests that the Y detection is an overdetected T-wave. Therefore the Y detection is discarded and the interval data between X and Z is corrected.

In the examples of FIGS. 11-13 and 14A-B, if a likely overdetection is not discarded, resulting in data correction, the likely overdetection may instead be marked as a suspect detection. In an example, suspect detections are treated as unreliable, both as indicators of cardiac activity and as endpoints for intervals that can be used in rate analysis. If the likely overdetection is marked as a suspect detection, the suspect detection and each of the preceding and following intervals around the suspect detection are removed from analysis entirely.

FIG. 15 shows a method of analysis for identifying shockable detected events and treatable rhythms. FIG. 15 shows the overarching structure of an analysis method by including the steps of event detection 402, which is followed by waveform appraisal 404 and beat qualification 406. In particular, event detection 402 will typically include monitoring a captured signal to detect signal amplitude changes that indicate cardiac events. Once cardiac events are captured at block 402, waveform appraisal 404 can occur. During waveform appraisal 404, the characteristics of the signal associated with a detected event are analyzed to identify and eliminate detected events that are likely caused by noise or artifacts.

Next, detected events that pass waveform appraisal 404 undergo beat qualification 406, during which detected events are analyzed to determine whether they display morphology or interval characteristics that indicate accurate detection. This may include the correlation analyses shown above, and/or analysis of intervals or combinations of the two, for example analysis to eliminate wide complex double detection can use detected event proximity and shape characteristics to identify likely overdetections. Some further discussion appears in U.S. patent application Ser. No. 12/399,914, titled METHODS AND DEVICES FOR ACCURATELY CLASSIFYING CARDIAC ACTIVITY, and published as US Patent Application Publication Number 2009-0259271.

The architecture then turns to rhythm classification, which can begin by consideration of rate at block 408. If the rate is low, then an individual detection is marked as "Not Shockable" as indicated at 410. Alternatively, if the rate is very high, it is considered to indicate ventricular fibrillation (VF) and therefore is marked as "Shockable," as shown at 412. Between these low and VF bands of rates is a ventricular tachycardia (VT) zone, and rates in the VT zone are analyzed using what will be referred to as Detection Enhancements, as shown at 414.

An example of a Detection Enhancement is as follows:

1. Compare to static template: If Match, not shockable; else
2. Compare to dynamic template: If no Match, shockable event; else
3. Compare to QRS width threshold: If wide, shockable, else not shockable.

Where the dynamic template can be any of the following:
  a) An average of several previous detections that correlate to one another;
  b) A set of individual events, for example {N−1 . . . N−i} wherein matching some or all of the individual events counts as matching the dynamic template;

c) A continually updated template.

The QRS width threshold noted above may be applied in various ways that can be tailored to the method of QRS width measurement used in a given system and/or that may be tailored to an individual patient. In one example, the following rules apply to QRS width:

x) QRS width, during analysis, is calculated as the duration from the start of the longest monotonic segment captured during refractory before the fiducial point to the end of the longest monotonic segment captured during refractory after the fiducial point;

y) QRS width threshold is measured for the patient during a programming session, with a maximum allowed value of 113 ms; and z) QRS width during analysis is considered wide if it is at least 20 ms longer than the QRS width threshold.

These rules x), y) and z) are tailored to one particular embodiment and may vary depending on the system used.

Following the marking of events as Not Shockable 410 or Shockable 412, an X/Y counter condition is applied as indicated at 416. The X/Y counter condition analyzes the number of Shockable events, X, that are marked during a previous set, Y, of detected events that pass both waveform appraisal 404 and beat qualification 406. The ratio applied, and set size used, may vary. One embodiment applies an 18/24 X/Y counter condition at 416. Other embodiments use ratios as 8 or 9 out of 12, 12 or 13 out of 16, 24/32, etc.

If the X/Y condition is not met, no shock will be delivered, as shown at 418. If the X/Y condition is met, then the method may proceed to a charge confirmation block 420. For example, some embodiments require that the X/Y ratio/set size be met for a selected number of consecutive events, and this condition may be tested in charge confirmation 420. Another example condition is to determine whether a set, N, of immediately preceding detected events are all Shockable, or all have intervals that are sufficiently short to support a conclusion that the detected arrhythmia is ongoing. Other factors may also be applied in charge confirmation, for example, by observing whether overdetection has been recently noted (which may suggest that therapy should be delayed to ensure that the "arrhythmia" is not a manifestation of overcounting), or observing whether consistent long intervals have been detected (potentially suggesting spontaneous conversion to normal rhythm by the patient). For example, charge confirmation 420 may also include methods such as those shown in commonly assigned and copending U.S. patent application Ser. No. 11/042,911, titled METHOD FOR ADAPTING CHARGE INITIATION FOR AN IMPLANTABLE CARDIOVERTER-DEFIBRILLATOR, published as US Patent Application Publication Number 2006-0167503, the disclosure of which is incorporated herein by reference.

The Charge and Shock block 422 is reached if Charge Confirmation 420 is passed. Typically the process of charging takes some period of time, and so the method 400 may iterate several times before charging is completed. Some or all of the analysis used to reach an initial determination that Charging should start may be repeated during this process. Finally, if treatable conditions persist during charging, or are identified following charging, stimulus may be delivered.

With regard to the implantable system, various hardware features may be incorporated. For example, any suitable battery chemistry, such as a lithium ion battery, may be used. Therapy output can be created using a capacitive system to store energy until a stimulus level is reached using one or several capacitors. A charging circuit such as a flyback transformer circuit can be used to generate therapy voltages. Therapy can be delivered using, for example, an H-bridge circuit or a modification thereof. Dedicated or general purpose circuitry may be used to perform analysis functions. For example, a dedicated cardiac signal analog-to-digital circuit may be used, as well as a dedicated correlation analysis block, as desired, while other functions may be performed with a microcontroller. Static and dynamic memories may be provided and used for any suitable functions. These elements may all be components of the operational circuitry for the implantable cardiac stimulus system.

Those skilled in the art will recognize that the present invention may be manifested in a variety of forms other than the specific embodiments described and contemplated herein. Accordingly, departures in form and detail may be made without departing from the scope and spirit of the present invention.

What is claimed is:

1. A method of operation in an implantable cardiac stimulus (ICS) system comprising a canister housing operational circuitry for the ICS system, the canister having a canister electrode disposed thereon, and a lead having at least a first lead electrode disposed thereon, the canister electrode and the first lead electrode electrically coupled to the operational circuitry;

the method comprising:

detecting electrical events occurring within the patient, wherein the detected electrical events are separated by intervals;

calculating a cardiac rate using a set of the detected electrical events;

identifying one or more detected events as likely occurring due to overdetection;

analyzing intervals around the events identified as likely occurring due to overdetection to determine whether the likely overdetection is likely a T-wave and:

a) if the likely overdetection is likely a T-wave, correcting data relating to the overdetection to reduce calculated cardiac rate; or b) if the likely overdetection is unlikely to be a T-wave, disabling data correction methods in the ICS system for at least the likely overdetection;

determining whether a likely cardiac arrhythmia is occurring and, if so, determining whether stimulus is needed; and if stimulus is needed, delivering electrical stimulus to the patient from the ICS system.

2. The method of claim 1 wherein the step of analyzing intervals to determine whether the likely overdetection is likely a T-wave includes treating an period between the likely overdetection and an immediately preceding detected electrical event as a presumed QT period and treating a period between the detected electrical event that immediately precedes the likely overdetection and a detected electrical event immediately after the likely overdetection as a presumed RR interval, and applying an accepted relationship to the presumed RR interval and presumed QT period and:

if the accepted relationship is met for the presumed RR interval and presumed QT period, determining that the likely overdetection is likely to be a T-wave; or if the accepted relationship is not met for the presumed RR presumed interval and resumed QT period, determining that the likely overdetection is unlikely to be a T-wave.

3. The method of claim 2 wherein the accepted relationship defines an expected relationship between the RR interval and QT period of a cardiac cycle and is chosen from the group consisting of Bazett's formula, Friderica's formula, or a regression formula.

4. The method of claim 1 wherein the step of analyzing intervals to determine whether the likely overdetection is likely a T-wave includes comparing an interval between the likely overdetection and an immediately preceding detected event to a threshold and, if the threshold is exceeded, finding that the likely overdetection is not likely to be a T-wave.

5. A method of operation in an implantable cardiac system comprising a canister housing operational circuitry and a plurality of electrodes for sensing cardiac activity, the plurality of electrodes coupled to the operational circuitry and the operational circuitry comprising a processor and associated logic circuits for processing cardiac signals from the electrodes; the method comprising:
the operational circuitry detecting electrical events occurring within the patient by use of the electrodes, wherein the detected electrical events are separated by intervals;
the operational circuitry calculating a cardiac rate using a set of the detected electrical events;
the operational circuitry identifying one or more detected events as likely occurring due to overdetection;
the operational circuitry analyzing intervals around the events identified as likely occurring due to overdetection to determine whether the likely overdetection is likely a T-wave and:
a) if the likely overdetection is likely a T-wave, the operational circuitry correcting data relating to the overdetection to reduce calculated cardiac rate; or
b) if the likely overdetection is unlikely to be a T-wave, the operational circuitry disabling data correction methods in the ICS system for at least the likely overdetection; and
the operational circuitry determining whether a likely cardiac arrhythmia is occurring.

6. The method of claim 5 wherein the implantable cardiac system further comprises therapy delivery components for providing therapy to the patient, wherein the method further comprises:
If a likely cardiac arrhythmia is occurring, the operational circuitry determining whether stimulus is needed; and
if stimulus is needed, the implantable cardiac system using the therapy delivery components to deliver therapy to the patient.

7. The method of claim 5 wherein the step of the operational circuitry analyzing intervals to determine whether the likely overdetection is likely a T-wave includes treating an period between the likely overdetection and an immediately preceding detected electrical event as a presumed QT period and treating a period between the detected electrical event that immediately precedes the likely overdetection and a detected electrical event immediately after the likely overdetection as a presumed RR interval, and applying an accepted relationship to the presumed RR interval and presumed QT period and:
if the accepted relationship is met for the presumed RR interval and presumed QT period, determining that the likely overdetection is likely to be a T-wave; or
if the accepted relationship is not met for the presumed RR interval and presumed QT period, determining that the likely overdetection is unlikely to be a T-wave.

8. The method of claim 7 wherein the accepted relationship defines an expected relationship between the RR interval and QT period of a cardiac cycle and is chosen from the group consisting of Bazett's formula, Friderica's formula, or a regression formula.

9. The method of claim 5 wherein the step of the operational circuitry analyzing intervals to determine whether the likely overdetection is likely a T-wave includes comparing an interval between the likely overdetection and an immediately preceding detected event to a threshold and, if the threshold is exceeded, finding that the likely overdetection is not likely to be a T-wave.

10. An implantable cardiac system comprising a canister housing operational circuitry and a plurality of electrodes for sensing cardiac activity, the plurality of electrodes coupled to the operational circuitry and the operational circuitry comprising a processor and associated logic circuits for processing cardiac signals from the electrodes; the operational circuitry configured to perform the following to monitor cardiac activity of a patient:
the operational circuitry detecting electrical events occurring within the patient by use of the electrodes, wherein the detected electrical events are separated by intervals;
the operational circuitry calculating a cardiac rate using a set of the detected electrical events;
the operational circuitry identifying one or more detected events as likely occurring due to overdetection;
the operational circuitry analyzing intervals around the events identified as likely occurring due to overdetection to determine whether the likely overdetection is likely a T-wave and:
a) if the likely overdetection is likely a T-wave, the operational circuitry correcting data relating to the overdetection to reduce calculated cardiac rate; or
b) if the likely overdetection is unlikely to be a T-wave, the operational circuitry disabling data correction methods in the ICS system for at least the likely overdetection; and
the operational circuitry determining whether a likely cardiac arrhythmia is occurring.

11. The implantable cardiac system of claim 10 further comprising therapy delivery components for providing therapy to the patient coupled to the operational circuitry;
wherein the operational circuitry and therapy delivery components are configured such that the operational circuitry controls therapy delivery by the therapy delivery components;
wherein the operational circuitry is also configured to determine whether stimulus is needed in response to determining that a likely cardiac arrhythmia is occurring and, if so, directing the therapy delivery components to deliver therapy to the patient.

12. The implantable cardiac system of claim 10 wherein the operational circuitry is further configured such that:
the step of the operational circuitry analyzing intervals to determine whether the likely overdetection is likely a T-wave includes treating an period between the likely overdetection and an immediately preceding detected electrical event as a presumed QT period and treating a period between the detected electrical event that immediately precedes the likely overdetection and a detected electrical event immediately after the likely overdetection as a presumed RR interval, and applying an accepted relationship to the presumed RR interval and presumed QT period and:
if the accepted relationship is met for the presumed QT period and the presumed RR interval, determining that the likely overdetection is likely to be a T-wave; or
if the accepted relationship is not met, determining that the likely overdetection is unlikely to be a T-wave.

13. The implantable cardiac system of claim 12 wherein the operational circuitry is further configured such that the accepted relationship defines an expected relationship between the RR interval and QT period of a cardiac cycle and is chosen from the group consisting of Bazett's formula, Friderica's formula, or a regression formula.

14. The implantable cardiac system of claim 10 wherein the operational circuitry is further configured such that analyzing intervals to determine whether the likely overdetection is likely a T-wave includes comparing an interval between the likely overdetection and an immediately preceding detected event to a threshold and, if the threshold is exceeded, finding that the likely overdetection is not likely to be a T-wave.

* * * * *

UNITED STATES PATENT AND TRADEMARK OFFICE
CERTIFICATE OF CORRECTION

PATENT NO. : 8,600,489 B2  
APPLICATION NO. : 13/436448  
DATED : December 3, 2013  
INVENTOR(S) : Warren et al.

Page 1 of 1

It is certified that error appears in the above-identified patent and that said Letters Patent is hereby corrected as shown below:

On the Title Page

On page 4, Item (56) in column 2, under "Other Publications", line 14, delete "9,," and insert --9,--, therefor On page 4, Item (56) in column 2, under "Other Publications", line 19, delete "C," and insert --C.,--, therefor On page 4, Item (56) in column 2, under "Other Publications", line 22, delete "I,," and insert --I,--, therefor On page 4, Item (56) in column 2, under "Other Publications", line 26, delete "D," and insert --D.,--, therefor On page 4, Item (56) in column 2, under "Other Publications", line 31, delete "D," and insert --D.,--, therefor In the Claims In column 16, line 61, in claim 2, after "presumed RR", delete "presumed", therefor In column 16, line 61, in claim 25, delete "resumed" and insert --presumed--, therefor In column 17, line 38, in claim 6, delete "If" and insert --if--, therefor Signed and Sealed this  
Thirteenth Day of May, 2014

Michelle K. Lee  
*Deputy Director of the United States Patent and Trademark Office*